US008362243B2

(12) United States Patent
Lindhorst et al.

(10) Patent No.: US 8,362,243 B2
(45) Date of Patent: *Jan. 29, 2013

(54) METHOD FOR SELECTIVE LOCALIZATION OF ACTIVE AGENTS AT AND IN MITOCHONDRIA AND CORRESPONDING ACTIVE AGENTS

(75) Inventors: Thomas Lindhorst, Innsbruck (AT); Birgit Werner, Innsbruck (AT); Stefan Piper, Götzens (AT)

(73) Assignee: Ugichem Gesellschaft fuer Organische Chemie mbH, Innsbruck (AT)

( * ) Notice: Subject to any disclaimer, the term of this patent is extended or adjusted under 35 U.S.C. 154(b) by 711 days.

This patent is subject to a terminal disclaimer.

(21) Appl. No.: 12/446,860

(22) PCT Filed: Oct. 23, 2007

(86) PCT No.: PCT/EP2007/009187
§ 371 (c)(1),
(2), (4) Date: Jul. 16, 2009

(87) PCT Pub. No.: WO2008/049583
PCT Pub. Date: May 2, 2008

(65) Prior Publication Data
US 2010/0009895 A1 Jan. 14, 2010

(30) Foreign Application Priority Data
Oct. 24, 2006 (DE) .................. 10 2006 050 091

(51) Int. Cl.
*C07F 9/02* (2006.01)
*A61K 31/675* (2006.01)
(52) U.S. Cl. ............ 544/232; 514/1.1; 514/86; 514/148; 514/538
(58) Field of Classification Search ............... 514/2, 86, 514/148, 538, 1.1; 544/232
See application file for complete search history.

(56) References Cited

U.S. PATENT DOCUMENTS

| 7,105,648 B1 * | 9/2006 | Bock et al. .................. 536/23.1 |
| 2003/0022172 A1 | 1/2003 | Ulhmann et al. |
| 2005/0031651 A1 | 2/2005 | Gervais et al. |

FOREIGN PATENT DOCUMENTS

| WO | WO 99/37294 A | 7/1999 |
| WO | WO 00/52038 A | 9/2000 |
| WO | WO 2008/009470 A | 1/2008 |

OTHER PUBLICATIONS

Chinnery, P.F. et al.: "Peptide nucleic acid delivery to human mitochondria", *Gene Therapy*, Dec. 1999, vol. 6, No. 12, pp. 1919-1928.
Reddy, P. Hemachandra: "Mitochondrial Oxidative Damage in Aging and Alzheimer's Disease: Implications for Mitochondrially Targeted Antioxidant Therapeutics", *Journal of Biomedicine and Biotechnology*, vol. 2006, Article ID 31372, pp. 1-13.
Sheu, Shey-Shing, et al.: "Targeting antioxidants to mitochondria: A new therapeutic direction", *Biochimica et Biophysica Acta*, 1762 (2006) pp. 256-265.
Jauslin, Matthias L. et al.: "Mitochondria-targeted antioxidants protect Friedreich Ataxia fibroblasts from endogenous oxidative stress more effectively than untargeted antioxidants", *FASEB Journal*, vol. 17, Oct. 2003, pp. 1972-1974.
Jeong, Tae-Sook et al.: "Novel 3,5-diaryl pyrazolines and pyrazole as low-density lipoprotein (LDL) oxidation inhibitor", *Bioorganic & Medicinal Chemistry Letters*, 14 (2004) pp. 2719-2723.
Razumiene, J. et al.: "New bioorganometallic ferrocene derivatives as efficient mediators for glucose and ethanol biosensors based on PQQ-dependent dehydrogenases", *Journal of Organometallic Chemistry*, 668 (2003) pp. 83-90.
Weissig, Volkmar: "Mitochondrial-Targeted Drug and DNA Delivery", *Critical Reviews in Therapeutic Drug Carrier System*, 20(1) (2003) pp. 1-62.
Blaikie, Frances H. et al.: "Targeting Dinitrophenol to Mitochondria: Limitations to the Development of a Self-limiting Mitochondrial Protonophore", *Biosci Rep* (2006) 26, pp. 231-243.
Muratovska, Aleksandra et al.: "Targeting peptide nucleic acid (PNA) oligomers to mitochondria within cells by conjugation to lipophilic cations: implications for mitochondrial DNA replication, expression and disease", *Nucleic Acids Research*, 2001, vol. 29, No. 9, pp. 1852-1863.
Kofoed, Thomas et al.: "PNA Synthesis Using a Novel Boc/Acyl Protecting Group Strategy", *Journal of Peptide Science*, 7 (2001) pp. 402-412.
Breipohl, Gerhard et al.: "Novel Synthetic Routes to PNA Monomers and PNA-DNA Linker Molecules", *Tetrahedram*, vol. 53, No. 43, 1997, pp. 14671-14686.
Thomson, Stephen A. et al.: "Fmoc Mediated Synthesis of Peptide Nucleic Acids", *Tetrahedram*, vol. 51, No. 12, 1995, pp. 6179-6194.
Haaima, Gerald et al.: "Peptide Nucleic Acids (PNAs) Containing Thymine Monomers Derived from Chiral Amino Acids: Hybridization and Solubility Properties of D-Lysine PNA", *Angew Chem Int Ed Engl.*, 1996, 35, No. 17, pp. 1939-1942. Schollkopf, Ulrich et al.: "Asymmetric Synthesis of Various Non-Proteinogenic Amino Acid Methyl Esters (Functionalized in the Carbon Chain) and Amino Acids by the Bislactim Ether Method", *Lichigs Ann Chem.*, 1986, pp. 2150-2163.
Schick, Andreas et al.: "Synthesis of Phosphonate Analogues of Sphinganine-l-phosphate and Sphingosine-l-phosphate", *Tetrahedron*, vol. 51, No. 41, 1995, pp. 11207-11218.
Cortopassi, G.A. et al.: "Mitochondria in organismal aging and degeneration", *Biochimica et Biophysica Acta (BBA)—Bioenergetics*, vol. 1410, Issue 2, Feb. 9, 1999, Abstract Only.
Carew, Jennifer S. et al.: "Mitochondrial defects in cancer", *Molecular Cancer*, 2002, I:9, 12 pages.
Modica-Napolitano, Josephine, et al.: "Mitochondria as targets for detection and treatment of cancer", *expert reviews in molecular medicine*, Apr. 11, 2002, 19 pages.

\* cited by examiner

*Primary Examiner* — Shailendra Kumar
(74) *Attorney, Agent, or Firm* — Frommer Lawrence & Haug LLP; Ronald R. Santucci

(57) ABSTRACT

The present invention relates to novel methods for selective localization of active agents both at and in mitochondria within living cells, as well as corresponding active agents that penetrate through the cell membrane into the cells without further adjuvants and there can be localized both at and in mitochondria. These active agents are substituted with at least one monohydroxy mononitrophenyl rest or monohydroxy dinitrophenyl rest.

18 Claims, 2 Drawing Sheets

Fig. 1: HeLa cells with compounds of the general formula I according to the invention, substituted with one monohydoxy mononitrophenyl rest.

Line scan (dashed line)

Mitochondria (black points)

Cell nucleus

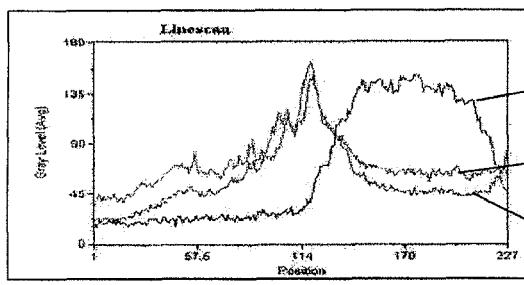

Signal intensity of the cell nucleus in the line scan

Signal intensity of MitoTracker in the line scan

Signal intensity of the compound of the general formula I according to the invention in the line scan Fig. 2: HeLa cells with compounds of the general formula I according to the invention, substituted with one monohydroxy mononitrophenyl rest.

Line scan (dashed line)

Mitochondria (black points)

Cell nucleus

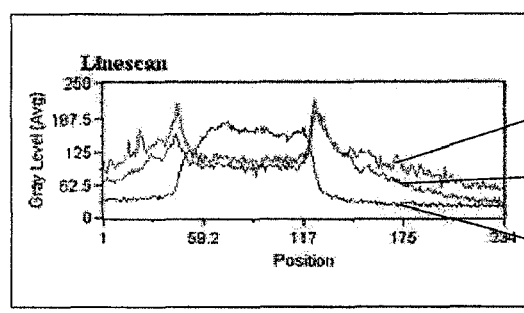

Signal intensity of MitoTracker in the line scan

Signal intensity of the compound of the general formula I according to the invention in the line scan Signal intensity of the cell nucleus in the line scan Fig. 3: HeLa cells with compounds of the general formula I according to the invention, substituted with one monohydroxy dinitrophenyl rest.
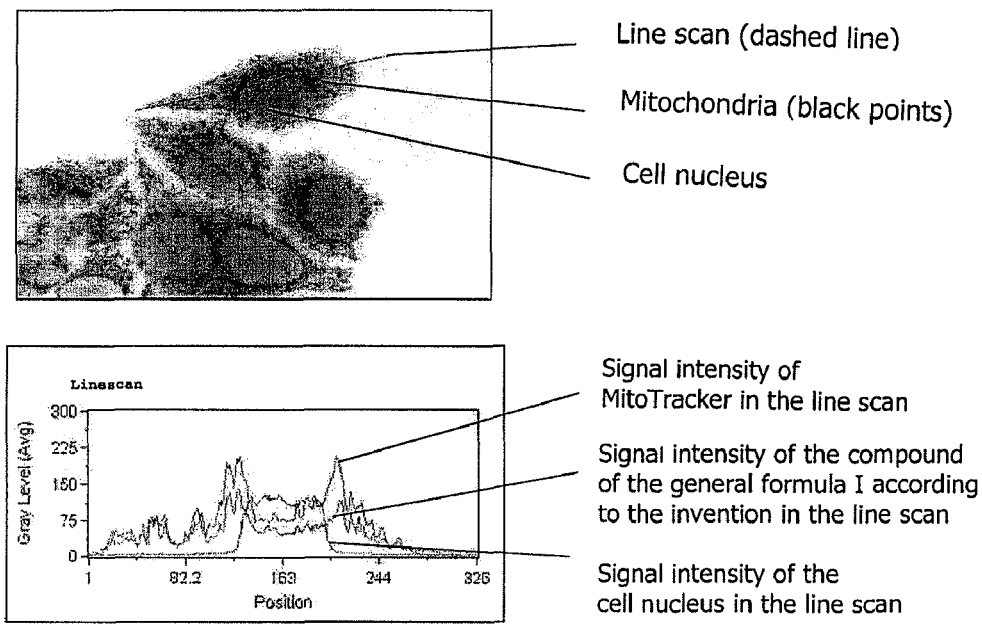
Fig. 4: 143B parental cells with compounds of the general formula I according to the invention, substituted with a monohydroxy dinitrophenyl rest
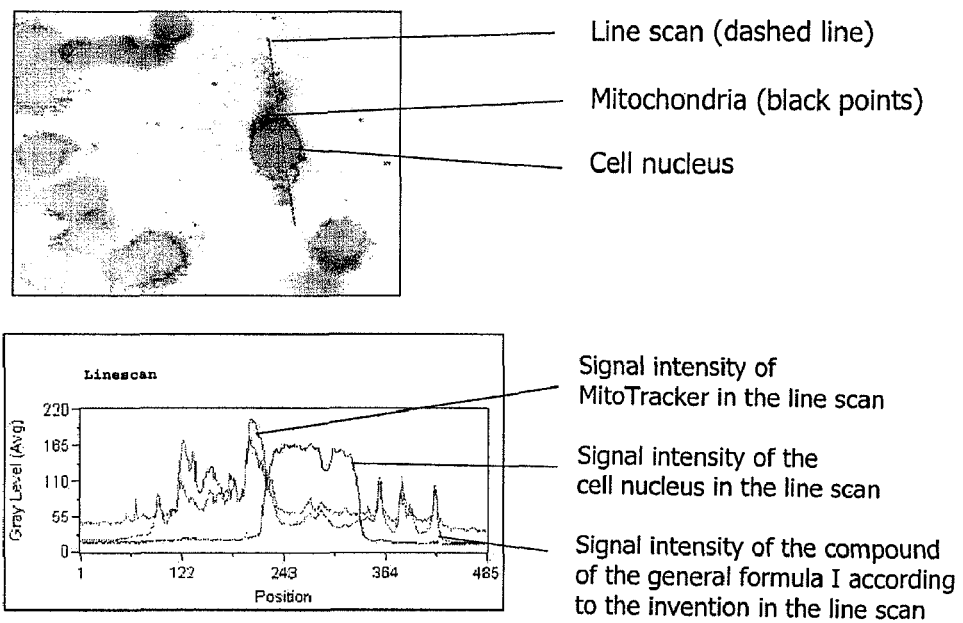

METHOD FOR SELECTIVE LOCALIZATION OF ACTIVE AGENTS AT AND IN MITOCHONDRIA AND CORRESPONDING ACTIVE AGENTS

This application is a 371 of PCT/EP2007/009187 filed on Oct. 23, 2007, published on May 2, 2008 under publication number WO 2008/049583 A which claims priority benefits from German Patent Application Number 10 2006 050 091 filed Oct. 24, 2006, the disclosure of which is incorporated herein by reference.

The present invention relates to novel methods for selective localization of active agents both at and in mitochondria within living cells as well as corresponding active agents which permeate through the cell membrane into the cells without further adjuvants and which there are localized selectively both at and in mitochondria.

The localization of active agents at or in mitochondria, respectively, means in the whole application the accumulation of active agents at or in mitochondria, respectively. The expression "localized" at or in mitochondria, respectively, means in the whole application "accumulated" at or in mitochondria, respectively.

Mitochondria are semiautonomous organelles of the cell. They possess their own genome (mtDNA) which codes—beside the nuclear genome—for a part of their proteins. The proteins encoded by the mitochondrion are transcribed, translated and synthesized also by the mitochondrion. Important metabolism pathways in the mitochondria serve for the energy generation, and therefore, are essential for the vitality of the cell.

Mitochondrial diseases comprise, for example, numerous hereditary diseases, cancer, diabetes, Parkinson's disease and arteriosclerosis. Among others, mitochondrial metabolism disorders are made responsible for the phenomena of aging, for example hardness of hearing or the decrease of vision. The phenomena of aging, for example, are also attributed to mutations or deletions, respectively, of the mitochondrial DNA. ("Mitochondria as targets for detection and treatment of cancer", Josephine S. Modica-Napolitano, Keshav K. Singh, *Expert Reviews in Molecular Medicine*, (02)00445-3a.pdf (short code: txt001ksb); 11 Apr. 2002, ISSN 1462-3994 ©2002 Cambridge University Press. "Mitochondrial defects in cancer", Jennifer S Carew, Peng Huang, *Molecular Cancer*, 2002, I:9; G. A. Cortopassi, Aliu Wong, *Biochimica et Biophysica Acta (BBA)-Bioenergetics*, 1999, 1410 (2), 183-193.).

The gene defects which form the basis of mitochondrial diseases range from sporadically occurring and purely maternally inherited point and length mutations of mtDNA up to autosomally dominantly or recessively, respectively, inherited forms upon mutations within the nuclear genome. Additionally, it is discussed that mutations in the mtDNA play also a role in polygenic diseases with complicated inheritance.

The characteristics of these diseases are the multiplicity of their clinical phenomena, the complexity of the diagnosis, and the therapy approaches which are available up to now only in a limited way. Thus, the investigation and diagnosis of distinct properties of mitochondria, for example the mutations of mitochondrial DNA or mitochondrial metabolism disorders, are an important precondition for the development of adequate active agents against mitochondrial diseases. The selective localization of active agents at mitochondria within cells is also an important aspect since thereby a high local concentration of active agents at the mitochondria is generated which finally results in an import of the active agents into the mitochondria.

Therefore it is an object of the present invention to provide a method whereby mitochondrial active agents, for example small molecules or antisense active agents, can be localized selectively within the cells both at and in mitochondria.

Mitochondrial active agents are substances that achieve an effectiveness both at and in mitochondria, such as an effectiveness in the treatment of mitochondrial diseases or an effectiveness in relation to diagnostic methods both at and in mitochondria.

Furthermore, it is an object of the present invention to provide antisense active agents that permeate through the cell membrane into the cells without further adjuvants and that are localized there selectively both at and in mitochondria in order to generate an antisense or an antigenomic effect in mitochondria.

These objects are solved by compounds of the general formula I:

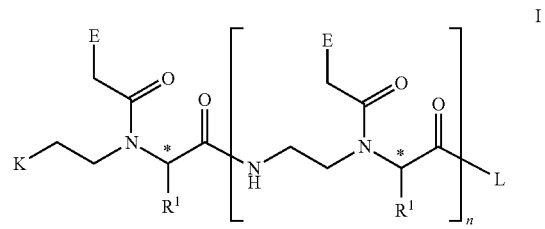

wherein n is an integer from 0 to 35, preferably from 1 to 28, more preferably from 9 to 28, most preferably from 13 to 20.

The rests K, L or $R^1$ independently of each other are substituted with at least one monohydroxy mononitrophenyl rest, preferably with a 4-hydroxy-3-nitrophenyl rest, further preferably with a 4-hydroxy-2-nitrophenyl rest, further preferably with a 3-hydroxy-6-nitrophenyl rest, or with a monohydroxy dinitrophenyl rest, preferably with a 3,5-dinitro-4-hydroxyphenyl rest, further preferably with a 2,5-dinitro-4-hydroxyphenyl rest, further preferably with a 2,4-dinitro-5-hydroxyphenyl rest, wherein the position of connection of the phenyl rests with the rests K, L or $R^1$ is defined as position 1, and additionally, the phenyl rest may be substituted with one or more fluorine, chlorine, bromine or iodine atoms, or with —COOH, —COOR$^8$, —CSOH, —CSOR$^8$, —COSH, —COSR$^8$, —CONH$_2$, —CONHR$^9$, —COR$^{10}$R$^{11}$, —OH, —OR$^8$, —SH, —SR$^8$, —NH$_2$, —NHR$^9$, —NR$^{10}$R$^{11}$, —NR$^{12}$NOH, —NOR$^{13}$, phosphonic acid ester functions or phosphonic acid functions, or with $C_1$-$C_6$ alkyl, $C_2$-$C_6$ alkenyl, $C_2$-$C_6$ alkinyl, $C_1$-$C_6$ heteroalkyl, $C_3$-$C_{10}$ cycloalkyl, $C_3$-$C_{10}$ heterocycloalkyl, $C_6$-$C_{10}$ aryl, $C_5$-$C_9$ heteroaryl, $C_7$-$C_{12}$ aralkyl or $C_2$-$C_{11}$ heteroaralkyl groups, wherein $R^8$, $R^9$, $R^{10}$, $R^{11}$, $R^{12}$ and $R^{13}$ independently of each other represent $C_1$-$C_6$ alkyl rests.

E independently of each other represents a hydrogen atom, a substituted or unsubstituted phenyl rest, a substituted or unsubstituted heterocyclic rest, a nucleobase, optionally substituted by protecting groups, for example a naturally occurring or non-naturally occurring nucleobase, or a DNA intercalator.

Preferably, each E independently of each other represents an adeninyl, cytosinyl, pseudoisocytosinyl, guaninyl, thyminyl, uracilyl or phenyl rest.

Each rest $R^1$ independently of each other represents a hydrogen atom or an optionally substituted alkyl, alkenyl, alkylaryl, aryl, heterocyclic or alicyclic rest having up to 20 carbon atoms, wherein at least one rest $R^1$ does not represent a hydrogen atom and is substituted with one or more phosphonic acid ester functions or phosphonic acid functions.

If the rest $R^1$ is not substituted with one or more phosphonic acid ester functions or phosphonic acid functions, it may independently of each other have also for example one or more side chains of a naturally occurring or non-naturally occurring amino acid, and preferably, an optionally substituted alkyl, alkenyl, alkylaryl, aryl, heterocyclic or alicyclic rest having up to 20 carbon atoms.

Preferably, each rest $R^1$ independently of each other comprises 1, 2, 3, 4, 5, 6, 7, 8, 9 or 10 carbon atoms.

Each rest $R^1$ independently of each other may be branched or not branched.

BRIEF DESCRIPTION OF THE DRAWINGS

FIG. 1 shows a line scan analysis through HeLa cells with compounds of the general formula I according to the invention, substituted with one monohydroxy mononitrophenyl group, and the corresponding signal intensities.

FIG. 2 shows a line scan analysis through HeLa cells with compounds of the general formula I according to the invention, substituted with one monohydroxy mononitrophenyl group, and the corresponding signal intensities.

FIG. 3 shows a line scan analysis through HeLa cells with compounds of the general formula I according to the invention, substituted with one monohydroxy dinitrophenyl group, and the corresponding signal intensities.

FIG. 4 shows a line scan analysis through 143B parental cells with compounds of the general formula I according to the invention, substituted with a monohydroxy dinitrophenyl group, and the corresponding signal intensities.

The expression "optionally substituted" relates in the whole application to groups in which one or more hydrogen atoms are replaced by fluorine, chlorine, bromine or iodine atoms, or by —COOH, —COOR$^8$, —CSOH, —CSOR$^8$, —COSH, —COSR$^8$, —CONH$_2$, —CONHR$^9$, —COR$^{10}$R$^{11}$, —OH, —OR$^8$, =O, —SH, —SR$^8$, =S, —NH$_2$, =NH, —NHR$^9$, —NR$^{10}$R$^{11}$, —NR$^{12}$NOH, —NOR$^{13}$ or —NO$_2$ groups, phosphonic acid ester functions or phosphonic acid functions. Furthermore, this expression relates to groups which are substituted with unsubstituted $C_1$-$C_6$ alkyl, $C_2$-$C_6$ alkenyl, $C_2$-$C_6$ alkinyl, $C_1$-$C_6$ heteroalkyl, $C_3$-$C_{10}$ cycloalkyl, $C_2$-$C_9$ heterocycloalkyl, $C_6$-$C_{10}$ aryl, $C_5$-$C_9$ heteroaryl, $C_7$-$C_{12}$ aralkyl or $C_2$-$C_{11}$ heteroaralkyl groups, wherein the rests $R^8$, $R^9$, $R^{10}$, $R^{11}$, $R^{12}$ and $R^{13}$ independently of each other represent $C_1$-$C_6$ alkyl rests.

Phosphonic acid ester functions may exhibit for example the formula —P(=O)(OV)$_2$ or —P(=O)(OV)(OH). In this context, each V independently of each other may represent an unsubstituted alkyl, alkenyl, alkylaryl, aryl, or alicyclic rest having up to 20 carbon atoms, more preferably, having up to 7 carbon atoms, and most preferably, a methyl, ethyl, cyclohexyl, or benzyl rest.

In the compounds according to the invention, the phosphonic acid functions may exhibit, for example, the formula —P(=O)(OH)$_2$.

Most preferably, each rest $R^1$ independently of each other is selected from a group of the formula —($C_1$-$C_{10}$)alkyl-[P(=O)(O—V)$_2$], wherein each V independently of each other represents a hydrogen atom, a methyl, ethyl, cyclohexyl or benzyl rest.

K represents a group of the formula —NR$^2$R$^3$, —N$^\oplus$R$^2$R$^3$R$^4$, —NR$^2$(CO)R$^3$ or —NR$^2$(CS)R$^3$, wherein R$^2$, R$^3$ and R$^4$ independently of each other represent a hydrogen atom, an alkyl, alkaryl, alkenyl or alkinyl rest, an amino protecting group, reporter ligand, fluorescence marker, intercalator, chelator, amino acid, peptide, protein, carbohydrate, lipid, steroid, fatty acid, oligonucleotide, quantum dot, FRET quencher (fluorescence resonance energy transfer quencher) or a polymer soluble or insoluble in water, wherein each of the above mentioned rests optionally may be substituted.

Preferably, K represents a —NH$_2$ function, a —NH(CO)CH$_3$ rest, a —NH(CO)—($C_1$-$C_{10}$)alkyl function, a —NH(CO)—($C_1$-$C_{10}$)alkaryl function, a —NH(CO)—($C_1$-$C_{10}$)alkenyl function, a —NH(CO)—($C_1$-$C_{10}$)alkinyl function, a group of the formula —NR$^2$R$^3$ or —N$^\oplus$R$^2$R$^3$R$^4$ or —NR$^2$(CO)R$^3$, wherein R$^2$, R$^3$ and R$^4$ independently of each other represent a hydrogen atom, a naturally occurring or non-naturally occurring amino acid, an amino acid or a peptide or an alkyl, alkaryl, alkenyl, or alkinyl rest which each are substituted or not with phosphonic acid ester functions or phosphonic acid functions, wherein each of the above mentioned rests may be substituted optionally.

L represents a group of the formula —NR$^5$R$^6$, —NR$^5$(CO)R$^6$, —NR$^5$(CS)R$^6$, —OR$^7$ or —SR$^7$ wherein R$^5$ and R$^6$ independently of each other represent a hydrogen atom, an alkyl, alkaryl, alkenyl, or alkinyl rest, reporter ligand, fluorescence marker, intercalator, chelator, amino acid, amino acid amide, peptide, peptide amide, protein, carbohydrate, lipid, steroid, fatty acid, oligonucleotide, quantum dot, FRET quencher (fluorescence resonance energy transfer quencher) or a polymer soluble or insoluble in water, and R$^7$ represents a hydrogen atom, an alkyl rest, reporter ligand, fluorescence marker, intercalator, chelator, amino acid, amino acid amide, peptide, peptide amid, protein, carbohydrate, lipid, steroid, fatty acid, oligonucleotide, quantum dot, FRET quencher or a polymer soluble or insoluble in water, wherein each of the above mentioned rests optionally may be substituted.

Preferably, L represents a —OH function, a —NH$_2$ function a —NH—($C_1$-$C_{10}$)alkyl function, —NH—($C_1$-$C_{10}$)alkaryl function, —NH($C_1$-$C_{10}$)alkenyl function, —NH—($C_1$-$C_{10}$)alkinyl function, a naturally occurring or non-naturally occurring amino acid, an amino acid, amino acid amide, peptide or peptide amid unit, all of which may be substituted or not with phosphonic acid ester functions or phosphonic acid functions, wherein each of the above mentioned rests optionally may be substituted.

In the whole application, alkyl rests preferably may have 1-6 carbon atoms, for example, they may represent methyl, ethyl, propyl or butyl groups. The expressions "aralkyl", "alkaryl", and "arylalkyl" in the whole application mean a group having an aliphatic and an aromatic moiety.

If $R^1$ does not represent a hydrogen atom, an asymmetric center (*) is generated due to the bond of the rest $R^1$ to the backbone of the general compound I at the bonding position. Therefore, at each asymmetric center, there exists an R configuration or an S configuration.

In this context, the configuration at the asymmetric center preferably is defined according to the Cahn-Ingold-Prelog rules, additionally provided that the priority of the ligands is always defined as follows: The nitrogen atom at the asymmetric center always receives priority 1. The carbon atom of the carboxyl group at the asymmetric center always receives priority 2. The carbon atom of the rest $R^1$ at the asymmetric center always receives priority 3. The hydrogen atom at the asymmetric center always receives priority 4.

According to the invention, the compounds of the general formula I exhibit at least one asymmetric center, wherein at least one rest $R^1$ is substituted with one or more phosphonic acid ester functions or phosphonic acid functions.

According to a further preferred embodiment of the invention, each second rest $R^1$ independently of each other corresponds to a side chain of a naturally occurring or non-naturally occurring amino acid, preferably to an optionally substituted alkyl, alkenyl, alkylaryl, aryl, heterocyclic or alicyclic rest having up to 20 carbon atoms, and at least one rest $R^1$ represents an optionally substituted alkyl, alkenyl, alkylaryl, aryl or alicyclic rest having up to 20 carbon atoms substituted with one or more phosphonic acid ester functions or phosphonic acid functions, wherein the remaining rests $R^1$ represent hydrogen atoms.

According to a further preferred embodiment of the invention, each third rest $R^1$ independently of each other corresponds to a side chain of a naturally occurring or non-naturally occurring amino acid, preferably to an optionally substituted alkyl, alkenyl, alkylaryl, aryl, heterocyclic or alicyclic rest having up to 20 carbon atoms, and at least one rest $R^1$ represents an optionally substituted alkyl, alkenyl, alkylaryl, aryl or alicyclic rest having up to 20 carbon atoms and is substituted with one or more phosphonic acid ester functions or phosphonic acid functions, wherein the remaining rests $R^1$ represent hydrogen atoms.

According to a further preferred embodiment of the invention, two, three or more adjacent rests $R^1$ independently of each other correspond to a side chain of a naturally occurring or non-naturally occurring amino acid, preferably to an optionally substituted alkyl, alkenyl, alkylaryl, aryl, heterocyclic or alicyclic rest having up to 20 carbon atoms, and at least one rest $R^1$ represents an optionally substituted alkyl, alkenyl, alkylaryl, aryl or alicyclic rest having up to 20 carbon atoms and is substituted with one or more phosphonic acid ester functions or phosphonic acid functions, wherein the remaining rests $R^1$ represent hydrogen atoms.

According to a further preferred embodiment of the invention, each rest $R^1$ independently of each other corresponds to the side chain of a naturally occurring or non-naturally occurring amino acid, preferably to an optionally substituted alkyl, alkenyl, alkylaryl, aryl, heterocyclic or alicyclic rest having up to 20 carbon atoms, and at least one rest $R^1$ represents an optionally substituted alkyl, alkenyl, alkylaryl, aryl or alicyclic rest having up to 20 carbon atoms and is substituted with one or more phosphonic acid ester functions or phosphonic acid functions.

According to a further preferred embodiment of the invention, one or more of the rests $R^1$ independently of each other exhibit at least one phosphonic acid ester function or phosphonic acid function.

According to further preferred embodiments of the present invention, the following applies:
If more than one asymmetric center and more than one optionally substituted rest $R^1$ having one or more phosphonic acid ester functions or phosphonic acid functions are present in the compound of the general formula I, at least 50% of the number of the asymmetric centers having rests with one or more phosphonic acid ester functions or phosphonic acid functions exhibit the R configuration, preferably 66%, more preferably 70%, more preferably 75%, more preferably 80%, more preferably 85%, more preferably 90%, more preferably 95%, and most preferably 100%.

According to alternative preferred embodiments of the present invention, the following applies:
If more than one asymmetric center and more than one optionally substituted rest $R^1$ having one or more phosphonic acid ester functions or phosphonic acid functions are present in the compound of the general formula I, at least 50% of the number of the asymmetric centers having rests with one or more phosphonic acid ester functions or phosphonic acid functions exhibit the S configuration, preferably 66%, more preferably 70%, more preferably 75%, more preferably 80%, more preferably 85%, more preferably 90%, more preferably 95%, and most preferably 100%.

In a further embodiment, at most 80% of the number of the rests $R^1$ are substituted with phosphonic acid ester functions or phosphonic acid functions, and the remaining rests $R^1$ represent hydrogen atoms.

In a further embodiment, at most 60% of the number of the rests $R^1$ are substituted with phosphonic acid ester functions or phosphonic acid functions, and the remaining rests $R^1$ represent hydrogen atoms.

In a further embodiment, at most 50% of the number of the rests $R^1$ are substituted with phosphonic acid ester functions or phosphonic acid functions, and the remaining rests $R^1$ represent hydrogen atoms.

In a further embodiment, at most 40% of the number of the rests $R^1$ are substituted with phosphonic acid ester functions or phosphonic acid functions, and the remaining rests $R^1$ represent hydrogen atoms.

In a further embodiment, at most 30% of the number of the rests $R^1$ are substituted with phosphonic acid ester functions or phosphonic acid functions, and the remaining rests $R^1$ represent hydrogen atoms.

In a further embodiment, at most 20% of the number of the rests $R^1$ are substituted with phosphonic acid ester functions or phosphonic acid functions, and the remaining rests $R^1$ represent hydrogen atoms.

In a further embodiment, at most 10% of the number of the rests $R^1$ are substituted with phosphonic acid ester functions or phosphonic acid functions, and the remaining rests $R^1$ represent hydrogen atoms.

In a further embodiment, at most 4% of the number of the rests $R^1$ are substituted with phosphonic acid ester functions or phosphonic acid functions, and the remaining rests $R^1$ represent hydrogen atoms.

In a further preferred embodiment of the invention, all asymmetric centers (*) of the general compound I exhibit the same configuration.

In a further preferred embodiment of the invention, all asymmetric centers (*) of the general compound I exhibit the S configuration.

In a further preferred embodiment of the invention, all asymmetric centers (*) of the general compound I exhibit the R configuration.

Furthermore, compositions according to the invention are disclosed which contain one or more compounds according to the invention, optionally in combination with usual adjuvants.

The synthesis of the compounds according to the general formula I is preferably carried out from enantiomerically pure monomers. During the synthesis of the compounds of the general formula I, individual asymmetric centers may change their prior defined configuration in a small percentage due to the chemical synthesis conditions. The maximum percentage of the compounds of the general formula I formed during the synthesis is however stereoisomerically pure. Also these compositions are able to fulfil the object of the invention.

A compound of the general formula I may be connected through the rests K and L as linkers with a second compound of the general formula I, wherein the rests are defined as above. The configuration at the asymmetric centers of the first compound of the general formula I is independent of the configuration of the asymmetric centers of the second compound of the general formula I that is connected by the linker. Thus, for example, all asymmetric centers of the first compound of the general formula I may exhibit the R configuration, and all asymmetric centers of the second connected compound of the general formula I may exhibit the S configuration. For example, also all asymmetric centers of the first compound of the general formula I may exhibit the R configuration, and all asymmetric centers of the second connected compound of the general formula I may exhibit the R configuration.

The linker especially serves for the purpose to adjust the distance between the two compounds of the general formula I in such a way that between the two compounds of the general formula I having a linker and the single stranded RNA or DNA, or the double stranded DNA, respectively, a reciprocal interaction can take place via the respective nucleobases.

As linkers, all known linkers and all linker molecules are suitable that are applied or applicable for this purpose. For example, such a linker may represent an optionally substituted alkyl chain, a peptide, an oligonucleotide or an oligomer that is composed of at least three units of 8-amino-3,6-dioxaoctanoic acid (eg1 units).

The number and the sequence of the rests $R^1$ substituted with a phosphonic acid ester function or phosphonic acid function, respectively, can be freely selected according to the invention. Thus, each, each second, each third, each fourth, each fifth, each sixth, each seventh, each eighth, each ninth, or each tenth rest $R^1$ for example may be substituted with a phosphonic acid ester function or phosphonic acid function, respectively. The substitutions with the phosphonic acid ester functions or phosphonic acid functions, respectively, can be regularly or exist at any positions.

Furthermore, also several rests $R^1$ may be substituted with a phosphonic acid ester function or phosphonic acid function, respectively, in a subsequent manner (adjacent alignment). In this context, in the compound of the general formula I, also more of these adjacent alignments may be contained.

However, for example only individual rests $R^1$ at any positions may be substituted with a phosphonic acid ester function or phosphonic acid function, respectively.

The positions with the individual subsequent rests $R^1$ substituted with a phosphonic acid ester function or phosphonic acid function, respectively, may be arbitrary.

In EP 1157031, compounds are described that are substituted with phosphonic acid ester functions or phosphonic acid functions, and thus, exhibit a good cell permeability.

In contrast to the compounds described in EP 1157031, the presently described compounds according to the invention are substituted additionally with at least one monohydroxy mononitrophenyl rest or monohydroxy dinitrophenyl rest.

In case of these compounds according to the invention, the inventors assessed a surprising selective localization both at and in mitochondria within living cells. The compounds according to the invention can evolve their effectiveness by a surprisingly strong antisense or antigenomic effect within the mitochondria after their selective localization both at and in mitochondria.

For the assessment of the localization both at and in mitochondria, the compounds according to the invention have been labeled with the fluorescent dye biotin in order to be able to detect these compounds in experiments for cell permeability with a confocal microscope due to the green fluorescence within the cells. For staining of the mitochondria, commercially available "MitoTracker" was used, and by using thereof, the mitochondria can be recognized by a confocal microscope due to the red fluorescence. Simultaneously, the cell nucleus was identified by "DAPI"-staining due to his blue fluorescence. The cells were incubated with a 10 µM solution of biotin labeled compounds according to the invention for 24 hours, and thereafter analyzed by the confocal microscope. In this context, different line scans were measured through the cells.

The line scan analyses in the FIGS. 1-4 through the HeLa cells or parental cells 143B, respectively, exhibit the signal intensities of the compounds of the general formula I, of the mitochondria, and of the cell nuclei. By means of the parallel signal intensities of the compounds of the general formula I according to the invention having a monohydroxy mononitrophenyl rest (FIGS. 1-2) or monohydroxy dinitrophenyl rest (FIGS. 3-4), respectively, and the mitochondria, the selective localization of the compounds of the general formula I both at and in the mitochondria can be clearly recognised. In the cell nucleus, however, no compounds according to the invention can be recognized. At this, the compounds according to the invention exhibit a comparable selectivity in respect of the localization both at an in the mitochondria like the commercially available staining reagent for mitochondria, "MitoTracker".

The compounds according to the invention exhibit also an surprisingly strong antisense and antigenomic effect within the mitochondria. A compound according to the invention directed to the expression of the mitochondrial protein COX1 reduces the protein level of COX1 after 3 days to 71%, and after 9 days to 20% in HeLa cells at a concentration of 10 µM, compared with untreated HeLa cells. In addition to a time dependent effect, also a concentration dependent effect can be observed. Thus, for example after 9 days of incubation, the protein level of COX1 is reduced to 55% at a concentration of 2.5 µM, and to 80% even at a concentration of 500 nM.

Also the number of copies of mitochondrial DNA in HeLa cells is reduced by the treatment with the compounds according to the invention (with an anti COX1 sequence) in a time and concentration dependent manner. Whereas at a concentration of 10 µM after 3 days still no effect can be assessed, a reduction of mtDNA to 81% after 6 days, and to 62% after 9 days can be observed. These values should be compared with untreated HeLa cells, or with HeLa cells treated with a compound according to the invention, but having no complementary sequence to the mtDNA (negative control), respectively.

For the HeLa cells treated with the compounds according to the invention (with an anti COX1 sequence) at different concentrations, the copy number of mtDNA is reduced for example after 9 days to 62% at 10 µM, to 82% at 2.5 µM, and to 83% at 500 nM.

Therefore, the compounds according to the invention are clearly superior to the known peptide nucleic acids coupled with a triphenylphosphonium rest (A. Muratovska, R. N. Lightowlers, R. W. Taylor, D. M. Turnbull, R. A. J. Smith, J. A. Wilce, S. W. Martin, M. P. Murphy, *Nucleic Acid Research*, 2001, Vol. 29, No. 9, 1852-1863). The molecules described in this publication exhibit a bond to mitochondrial DNA in cell free systems only. Additionally, these molecules are indeed able to permeate the outer cell membrane of a cell and to attach to mitochondria, however, they exhibit no effectiveness in the mitochondria within cells, such as an antisense or antigenomic effect.

The compounds of the general formula I having no monohydroxy mononitrophenyl rest or monohydroxy dinitrophenyl rest at the substituents K, L or $R^1$ are distributed either equally within the cells, or they attach to other cell compartments different from mitochondria. Surprisingly, the substitution of the compounds of the general formula I with a monohydroxy mononitrophenyl rest or with a monohydroxy dinitrophenyl rest results in a selective localization of these mitochondrial active agents both at and in mitochondria.

Thereby, the present invention provides also a method by which compounds, for example compounds that can permeate through the outer cell membrane into the interior of the cell with or without the help of transfection reagents at an extracellular concentration of less than 50 μM, are localized by the covalent coupling with a monohydroxy mononitrophenyl rest or with a monohydroxy dinitrophenyl rest selectively both at and in mitochondria within cells, in order to be capable of evolving their effectiveness at or in mitochondria subsequently.

For example, the method comprises also the covalent coupling of a monohydroxy mononitrophenyl rest or a monohydroxy dinitrophenyl rest (optionally through a linker Linker M) to an active agent capable of oxidation or reduction, such as an antioxidant, in order to obtain an active agent selectively directed to mitochondrial diseases.

On the basis of these methods, the invention provides further compounds of the general formula V:

Z-M-P    V wherein
Z represents a functional group capable of oxidation or reduction,
M represents a linker group, and
P represents a monohydroxy mononitrophenyl rest or a monohydroxy dinitrophenyl rest.

Preferably, Z represents a group of the general formula VI, VII, VIII or IX

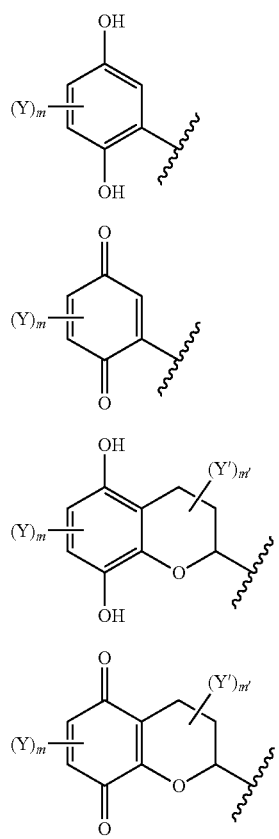

wherein m and m' represent an integer from 0 to 3.

Each Y and Y' independently of each other represent an alkoxy, thioalkyl, haloalkyl, halogen, amino, nitro or an optionally substituted alkyl or aryl rest, or, if m is equal to 2 or 3, two rests Y together may form one or two or three aliphatic, heterocyclic (a hetero atom is O, S or N) or aromatic rings, which are condensed with the aryl ring.

Preferably, each Y and Y' independently of each other represent a methyl or methoxy group.

Preferably, M represents a branched or non-branched, optionally substituted alkyl, alkenyl, alkinyl or alkylaryl chain, having optionally also a carboxylic acid ester, ether, amine or a carboxylic acid amid function as component of these chain, wherein M has up to 30 carbon atoms in total, more preferably M represents —$(CH_2)_p$—, wherein p represents an integer from 1 to 20, most preferably, M represents a ethyl, propyl, butyl, pentyl, hexyl, heptyl, octyl, nonyl or decyl chain.

Most preferably, Z represents a group of the formula:

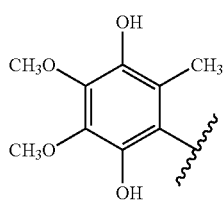

or a group of the formula:

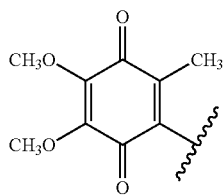

or a group of the formula:

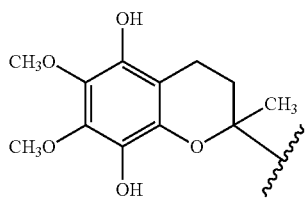

or a group of the formula:

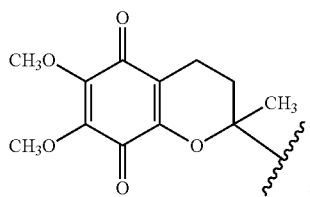

The compounds according to the invention and the method according to the invention are therefore appropriate for the treatment of mitochondrial diseases as well as for diagnostic purposes in connection with mitochondria. These include for example hereditary diseases, cancer, Parkinson's disease or diabetes. The compounds according to the invention may be employed also as anti-aging agents.

The use of the compounds according to the invention for the preparation of medicaments for the prevention and/or the treatment of diseases is also a subject matter of the present invention. Generally, the compounds according to the invention are administered using known and acceptable modes, either individually or in combination with any other therapeutic agent. For example, the administration can be applied by one of the following pathways: orally, for example as dragées, coated tablets, pills, semi-solids, soft and hard capsules, solutions, emulsions or suspensions; parenterally, for example as injectable solution; rectally as suppositories; by inhalation, for example as a powder formulation or spray, transdermally or intranasally. For the production of such tablets, pills, semi-solids, coated tablets, dragées and hard gelatin capsules, the therapeutically useable product may be mixed with pharmacologically inert inorganic or organic drug carrier substances, for example with lactose, sucrose, glucose, gelatin, malt, silica gel, starch or derivatives thereof, talkum, stearic acid or salts thereof, and fatless powdered milk etc. For the production of soft capsules, drug carrier substances, such as vegetable oils, petroleum, animal or synthetic oils, waxes, fats, polyols, may be used. For the production of fluid solutions and syrups, drug carrier substances, such as water, alcohols, aqueous salt solution, aqueous dextrose, polyols, glycerol, vegetable oils, petroleum, animal or synthetic oils, may be used. For suppositories, drug carrier substances, such as vegetable oils, petroleum, animal or synthetic oils, waxes, fats and polyols may be used.

For aerosol formulations, compressed gases suitable for this purpose, such as oxygen, nitrogen, chlorofluoro hydrocarbons, fluoro hydrocarbons, chloro hydrocarbons and carbon dioxide, may be used. The pharmaceutically usable agents may also contain additives for conservation, stabilization, emulsifiers, sweeteners, flavors, salts for changing the osmotic pressure, buffer substances, additives for coating and antioxidants.

The compounds of the general formula I according to the invention may be produced for example by methods described in the literature by a reaction of compounds of the general formula II in a manner known per se (for example L. Christensen, R. Fitzpatrick, B. Gildea, K. H. Petersen, H. F. Hansen, T. Koch, M. Egholm, O. Buchardt, P. E. Nielsen, J. Coull, R. H. Berg, *J. Pept. Sci.* 3, 1995, 175-183. T. Koch, H. F. Hansen, P. Andersen, T. Larsen, H. G. Batz, K. Otteson, H. Örum, *J. Pept. Res.* 49, 1997, 80-88. F. Bergmann, W. Bannwarth, S. Tam, *Tetrahedron Lett.* 36, 1995, 6823-6826).

The introduction of monohydroxy mononitrophenyl rests or monohydroxy dinitrophenyl rests as substituents into the compounds according to the invention may be carried out for example by the coupling of the compounds of the general formula III or IV to the amine function in the rests K, L or $R^1$.

III

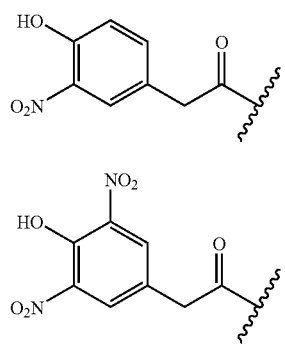

IV

In the following, the compound of the general formula III is abbreviated as MNPA ("MonoNitro-hydroxy-Phenyl-Acetat"), and the compound of the general formula IV is abbreviated as DNPA ("DiNitro-hydroxy-Phenyl-Acetat").

In the compounds of the general formula II

II

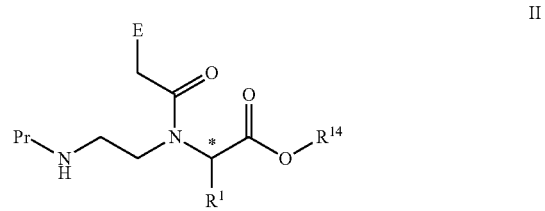

the rest $R^{14}$ represents for example a hydrogen atom or an allyl, benzyl, ethyl, or methyl rest, or a soluble or insoluble polymer.

Pr represents a hydrogen atom or a cleavable amine protecting group. The amine protecting group has to be selectively cleavable in the presence of the nucleobase protecting groups. Preferably, Pr represents a hydrogen atom, an oxocarbamate or thiocarbamate protecting group, most preferably, Pr represents a hydrogen atom or a Fmoc, Boc, Cbz, Mmt or a Bhoc protecting group.

E and the rest $R^1$ are as defined above.

The asymmetric center (*) which the rest $R^1$ binds to, may exhibit the R or S configuration.

For example, the compounds of the general formula II may be produced according to the following method.

Production of the compounds of the general formula II with R configuration at the asymmetric center:

Reaction Step 1:

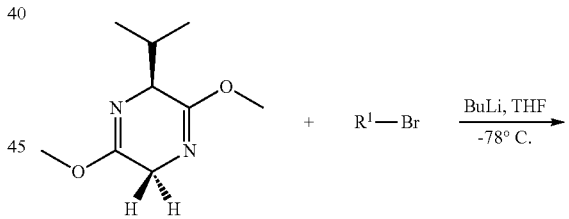

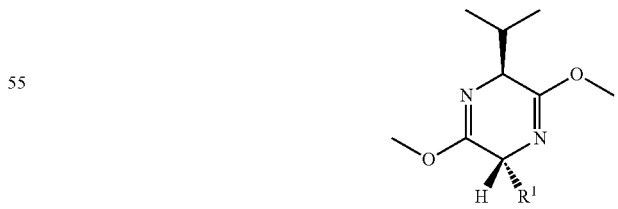

Starting from the S configuration of the pyrazine educt, the procedure may be carried out for example as described in the literature (U. Schöllkopf, U. Busse, R. Lonsky, R. Hinrichs, Liebigs Ann. Chem. 1986, 2150-2163; A. Schick, T. Kolter, A. Giannis, K. Sandhoff, Tetrahedron 51, 1995, 11207-11218).

Reaction Step 2:

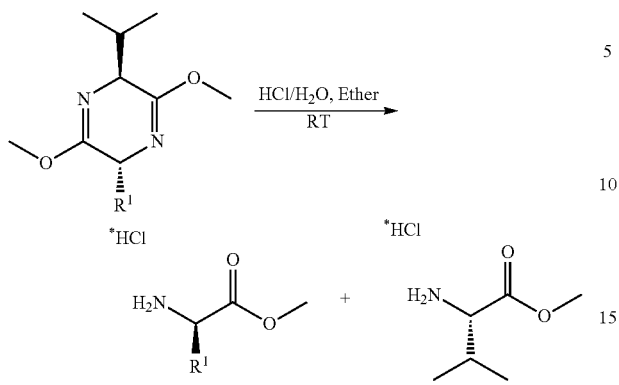

For example, the procedure can be carried out as described in the literature (U. Schöllkopf, U. Busse, R. Lonsky, R. Hinrichs, Liebigs Ann. Chem. 1986, 2150-2163).

Reaction Step 3:

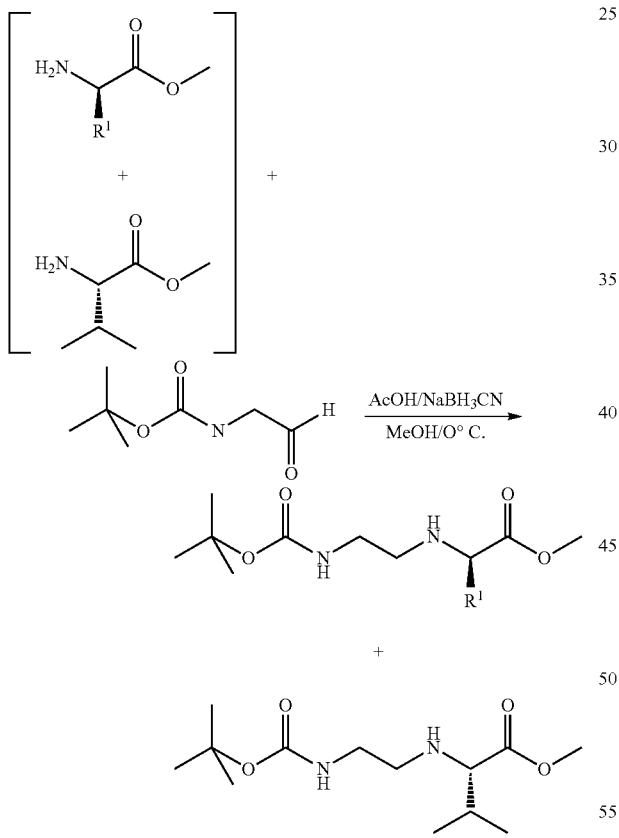

After releasing the amines from their hydrochlorides by a base (for example $NaHCO_3$, $NH_3$), the mixture of the product from reaction step 2 may be used in the following reaction. This reaction, a reductive amination, can be carried out as described in the literature (G. Haaima, A. Lohse, O. Buchardt, P. E. Nielsen, *Angew. Chem. Int. Ed. Engl.* 35, 1996, No 17, 1939-1942). Instead of sodium cyanoborohydride, also other reducing agents, for example hydrogen and a catalyst (for example Pd/C), can be used. The reaction products are separated by chromatography.

Reaction Step 4:

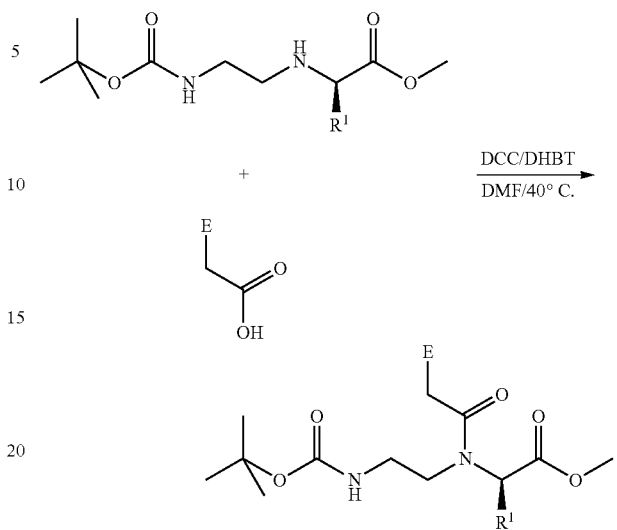

The procedure can be carried out as described in the literature (G. Haaima, A. Lohse, O. Buchardt, P. E. Nielsen, Angew. Chem. Int. Ed. Engl. 35, 1996, No 17, 1939-1942). In this context, also other coupling reagents may be used instead of DCC/DHBT. The production of the compound $E-CH_2-COOH$ (for example $C(PG)-CH_2-COOH$, $A(PG)-CH_2-COOH$, $G(PG)-CH_2-COOH$ or $T-CH_2-COOH$, $J(PG)-CH_2-COOH$, wherein A=adeninyl, C=cytosinyl, G=guaninyl, T=thyminyl, J=pseudoisocytosinyl, PG=protecting group, such as benzyloxycarbonyl (Z), benzyl (Bzl), acetyl (Ac) or anisoyl (An)) can be carried out as described in the literature (S. A. Thomson, J. A. Josey, R. Cadilla, M. D. Gaul, F. C. Hassmann, M. J. Lazzio, A. J. Pipe, K. L. Reed, D. J. Ricca, R. W. Wiether, S. A. Noble, *Tetrahedron* 51, 1995, 6179-6194). Further possible protecting groups are also described in the literature (G. Breitpohl, D. W. Will, A. Peymann, E. Uhlmann, Tetrahedron 53, 1997, 14671-14686; T. Kofoed, H. F. Hansen, H. Orum, T. Koch, *J. Peptide Sci.*, 7, 2001, 402-412).

Reaction Step 5:

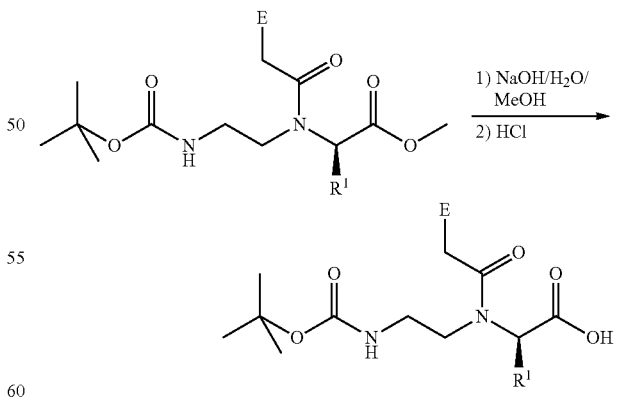

The procedure can be carried out as described in the literature (G. Haaima, A. Lohse, O. Buchardt, P. E. Nielsen, Angew. Chem. Int. Ed. Engl. 35, 1996, No 17, 1939-1942).

For a more simple description of the compounds of the general formula II which are generated as products in the reaction step 5, the following abbreviations are used:

If for example A(PG)-CH$_2$—COOH is used in reaction step 5, the corresponding compound of the general formula II having an asymmetric center is obtained. This compound is abbreviated here generally as A$^R$(PG). In this context, the abbreviation A means the nucleobase in the compound of the general formula II having an asymmetric center, the raised R means the R configuration of the compound, and the abbreviation PG means the protecting group at the nucleobase. If for example phenylacetic acid is used in reaction step 5, a compound of the general formula II having an asymmetric center is obtained that is abbreviated as P$^R$.

The corresponding compounds of the general formula II having no asymmetric center (R$^1$=H) are abbreviated analogically to the compounds of the general formula II having an asymmetric center, with the difference that instead of the capital letter for the nucleobase and the raised letter for the configuration (for example A$^R$), the respective small letter a is used. For example, a compound of the general formula II without an asymmetric center having a PG protected C as nucleobase is abbreviated as c(PG).

For the production of the compounds of the general formula II having an S configuration at the asymmetric center, the pyrazine educt having an R configuration is used in reaction step 1, and the reaction steps 1 to 5 are performed analogically. Then, for example a compound of the general formula II is obtained that is abbreviated as A$^S$(PG).

The compounds according to the invention can be produced for example via solid phase synthesis by reaction of the compounds of the general formula II in a manner known per se. According to the solid phase synthesis, the protecting groups at the nucleobases are cleaved so that compounds of the general formula II are obtained which are abbreviated as follows:

For example, a compound according to the invention that is produced exclusively from compounds of the general formula II having an asymmetric center with R configuration, and that is coupled with MNPA-OH in the final step and thereafter is cleaved as a primary amide from the resin, is abbreviated as MNPA-A$^R$C$^R$G$^R$G$^R$T$^R$C$^R$G$^R$G$^R$C$^R$G$^R$A$^R$A$^R$C$^R$A$^R$T$^R$-NH$_2$.

For example, a compound according to the invention that is produced from compounds of the general formula II having an asymmetric center with R configuration and from compounds of the general formula II having no asymmetric center, and that is coupled with MNPA-OH in the final step and thereafter is cleaved as a primary amide from the resin, is abbreviated as MNPA-A$^R$cG$^R$gT$^R$cG$^R$gC$^R$gA$^R$aC$^R$aT$^R$-NH$_2$.

For example, a compound according to the invention that is produced exclusively from compounds of the general formula II having an asymmetric center with S configuration, and that is coupled with DNPA-OH in the final step and thereafter is cleaved as a primary amide from the resin, is abbreviated as DNPA-A$^S$C$^S$G$^S$G$^S$T$^S$C$^S$G$^S$G$^S$C$^S$G$^S$A$^S$A$^S$C$^S$A$^S$T$^S$-NH$_2$.

For example, a compound according to the invention that is produced exclusively from compounds of the general formula II having an asymmetric center with S configuration and from compounds of the general formula II having no asymmetric center, and that is coupled in the final step with DNPA and thereafter is cleaved as a primary amide from the resin, is abbreviated as DNPA-A$^S$cG$^S$gT$^S$cG$^S$gC$^S$gA$^S$aC$^S$aT$^S$-NH$_2$.

For example, a compound according to the invention that is produced exclusively from compounds of the general formula II having an asymmetric center with R configuration and from compounds of the general formula II having no asymmetric center at a Boc-Gly-PAM-MBHA resin, and that is coupled with DNPA in the final step and thereafter is cleaved as a primary amide from the resin, is abbreviated as DNPA-tG$^R$c-C$^R$tA$^R$ggactc$^R$cA$^R$gC$^R$-Gly-NH$_2$.

For example, a compound according to the invention that is produced exclusively from compounds of the general formula II having an asymmetric center with R configuration and from compounds of the general formula II having no asymmetric center, from glycine, and from two amino acids, such as 4-(diethoxy-phosphoryl)-2-(tert.-butoxycarbonylamino) butyric acid (Boc-DEPABS) at a Boc-Gly-PAM-MBHA resin, and that is coupled with DNPA in the final step and thereafter is cleaved as a primary amide from the resin, is abbreviated as DNPA-(DEPABS)-2-Gly-tG$^R$cC$^R$tA$^R$ggact-c$^R$cA$^R$gC$^R$-Gly-NH$_2$.

For example, a compound according to the invention, that is produced from compounds of the general formula II having an asymmetric center with R configuration, from compounds of the general formula II having no asymmetric center, and from the chelator 1,4,7,10-tetraazacyclododecane-1,4,7,10-tetraacetic acid tri-tert.-butyl ester (DOTA) at a Boc-Gly-PAM-MBHA resin, and that is coupled with DNPA in the final step and thereafter is cleaved as a primary amid from the resin, is abbreviated as DNPA-DOTA-gG$^R$cT$^R$cG$^R$aA$^R$tA$^R$a-G$^R$gA$^R$gG$^R$-Gly-NH$_2$.

EXAMPLES

Example 1

Production of (2R,5S)-2-(2-(diethoxy-phosphoryl) ethyl)-2,5-dihydro-3,6-dimethoxy-5-isopropyl pyrazine

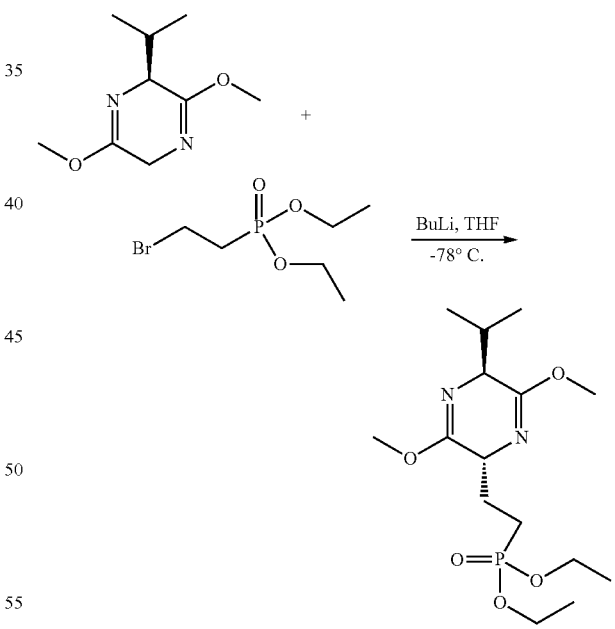

0.52 mol of (S)-2,5-dihydro-3,6-dimethoxy-2-isopropyl pyrazine are solved in 400 ml of absolute THF under argon and are cooled to −78° C. Under stirring, 200 ml of a 2.7 M solution of butyl lithium (in heptane) (0.54 mol) are added in drops and slowly. Subsequently, a solution of 0.52 mol diethyl-(2-bromethyl) phosphonate in 300 ml of absolute THF is added in drops and slowly during stirring, and the mixture is stirred for further 3 h at −78° C. Then, 11.7 ml (about 0.2 mol) anhydrous acetic acid are added slowly. The reaction mixture is allowed to warm up slowly to room temperature. The solvent is removed, and the residue is solved in 600 ml of diethyl ether and washed with 200 ml of water. The aqueous phase is still extracted three times with each 100 ml of diethyl ether. The combined ether phases are dried over MgSO$_4$, filtered and the solvent is removed in vacuo. The residue is solved in a mixture of diethyl ether and hexane (1:10) and filtered over a bed of silica gel. Thereafter, the non reacted educt is eluted with diethyl ether and hexane (1:5). Finally, the product is eluted with acetic acid ethyl ester.

Yield: about 70% of a yellow fluid $^1$H-NMR (CDCl$_3$): 0.71, 1.04 (d, 6H, CH(CH$_3$)$_2$), 1.33 (t, 6H, P(O)(OCH$_2$CH$_3$)$_2$), 1.68-2.25 (m, 4H, CHCH$_2$CH$_2$P), 3.65, 3.67 (s, 6H, OCH$_3$), 4.02 (m, 1H), 4.10-4.20 (m, 4H, P(O)(OCH$_2$CH$_3$)$_2$).

Example 2

Production of (2R,5S)-2-(8-(dibenzyloxy-phosphoryl)octyl)-2,5-dihydro-3,6-dimethoxy-5-isopropyl pyrazine Analogically to the production method in example 1, (2R, 5S)-2-(8-dibenzyloxyphosphoryl)octyl)-2,5-dihydro-3,6-dimethoxy-5-isopropyl pyrazine is produced starting from (S)-2,5-dihydro-3,6-dimethoxy-2-isopropyl pyrazine and dibenzyl-(8-bromooctyl) phosphonate.

Example 3

Production of (2S,5R)-2-(4-(dicyclohexyloxy-phosphoryl)but-2-enyl)-2,5-dihydro-3,6-dimethoxy-5-isopropyl pyrazine Analogically to the production method in example 1, (2S, 5R)-2-(4-(dicyclohexyloxy-phosphoryl)but-2-enyl)-2,5-dihydro-3,6-dimethoxy-5-isopropyl pyrazine is produced starting from (R)-2,5-dihydro-3,6-dimethoxy-2-isopropyl pyrazine and dicyclohexyl-(4-brom-but-2-enyl) phosphonate.

Example 4

Production of (2R)-2-[2-(tert.-butoxycarbonyl amino) ethyl]-amino-4-(diethoxy-phosphoryl) butyric acid methyl ester

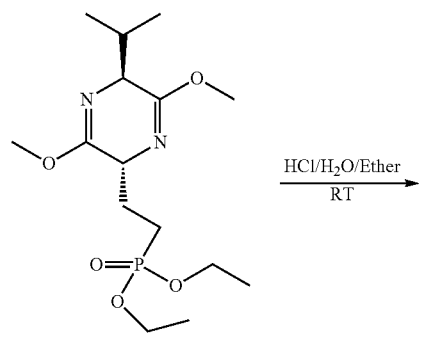

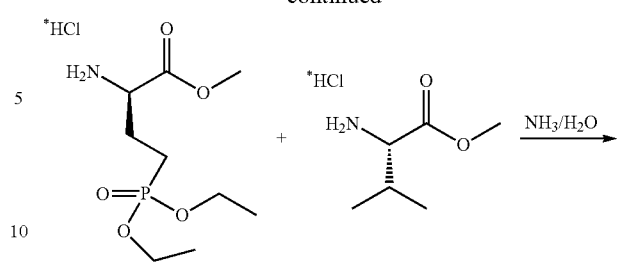

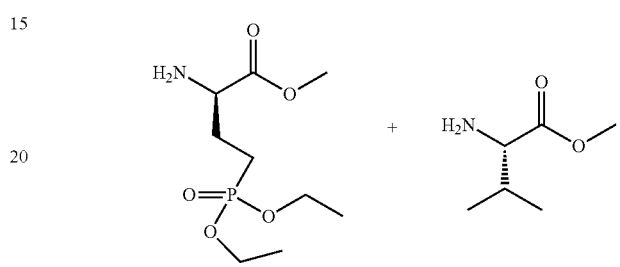

0.38 mol of (2R,5S)-2-(2-(diethoxy-phosphoryl)ethyl)-2,5-dihydro-3,6-dimethoxy-5-isopropyl pyrazine are solved in 400 ml of diethyl ether. To this solution, 1150 ml of a 1 N aqueous solution of hydrochloric acid are added. After 60 min, the reaction is completed and the ether is removed. If the product is to be stored, the water is also completely removed in vacuo. If the product is to be further reacted immediately, about one half of the water is removed by a rotating evaporator, and then the pH value of the reaction mixture is adjusted to 8-9 by ammonia solution. The basic solution is extracted six times with dichloromethane, wherein the pH value is controlled and optionally corrected each time. The dichloromethane phases are combined, dried over MgSO$_4$, and the solvent is removed in vacuo. The resulting yellow oil is immediately used in the following reaction, an reductive amination.

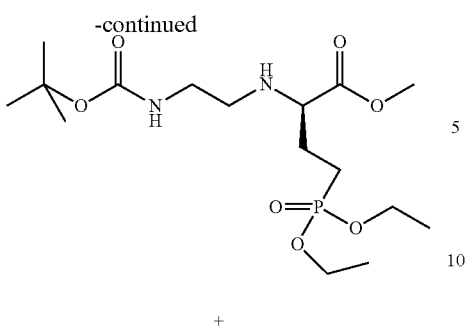

+

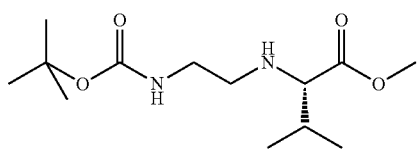

The yellow oil (a complete reaction is assumed) is solved in 600 ml of methanol and cooled to 0° C. Subsequently, 0.76 mol of N-Boc-aminoacetaldehyde are added. After stirring for 30 min at 0° C., at first 0.90 mol of anhydrous acetic acid and then 0.40 mol of sodium cyanoborohydride are added. The reaction mixture is stirred at 0° C., until the generation of gas is completed, and then the solvent is removed by a rotating evaporator. The residue is solved in acetic acid ethyl ester (about 600 ml), and further, washed once with saturated sodium bicarbonate solution (about 200 ml) and once with saturated sodium chloride solution (about 100 ml). The organic phase is dried over MgSO$_4$ and filtered. Subsequently, the solvent is removed in vacuo.

The further purification is carried out by SPE over a glass frit filled with silica gel. Impurities and unwanted products are at first eluted with a mixture of hexane and acetic acid ethyl ester (1:1), and then with pure acetic acid ethyl ester. The desired product is finally obtained by extraction with 10% methanol in dichloromethane.

After removing the solvent, about 75% of the product are obtained as a yellow viscous oil.

$^1$H-NMR (CDCl$_3$): 1.35 (t, 6H, P(O)(OCH$_2$CH$_3$)$_2$), 1.47 (s, 9H, C(CH$_3$)$_3$); 1.8-2.0 (m, 4H, CHCH$_2$CH$_2$P,), 2.5-2.6, 2.75-2.85, 3.0-3.4 (m, 4H, NCH$_2$CH$_2$N), 3.75 (s, 3H, OCH$_3$), 4.0-4.2 (m, 4H, P(O)(OCH$_2$CH$_3$)$_2$).

Example 5

Production of (2R)-2-[2-(tert.-butoxycarbonylamino) ethyl]-amino-10-(dibenzyloxy-phosphoryl) decanoic acid methyl ester Analogically to the production method in example 4, (2R)-2-[2-(tert.-butoxycarbonylamino) ethyl]-amino-10-(dibenzyloxy-phosphoryl)-decanoic acid methyl ester is produced starting from (2R,5S)-2-(8-(dibenzyloxy-phosphoryl)octyl)-2,5-dihydro-3,6-dimethoxy-5-isopropyl pyrazine.

Example 6

Production of (2S)-2-[2-(tert.-butoxycarbonylamino) ethyl]-amino-6-(dicyclohexyloxy-phosphoryl) hex-4-enoic acid methyl ester Analogically to the production method in example 4, (2S)-2-[2-(tert.-butoxycarbonylamino) ethyl]-amino-6-(dicyclohexyloxy-phosphoryl)-hex-4-enoic acid methyl ester is produced starting from (2S,5R)-2-(4-(dicyclohexyloxy-phosphoryl)-but-2-enyl)-2,5-dihydro-3,6-dimethoxy-5-isopropyl pyrazine.

Example 7

Production of (R)-2-([2-{N4-benzyloxycarbonylcytosin-1-yl}-acetyl]-[2-tert.-butoxycarbonylaminoethyl]-amino)-4-(diethoxy-phosphoryl) butyric acid methyl ester

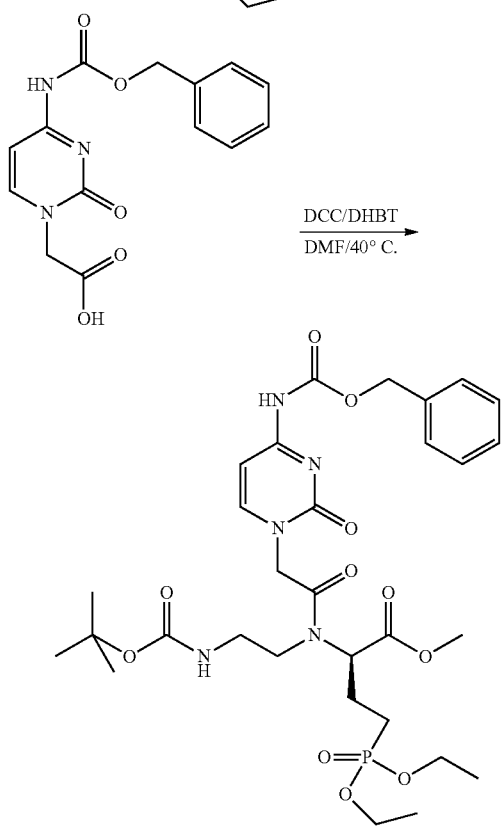

To a stirred solution of 30.96 mmol of 4-N-(benzyloxycarbonyl)-cytosin-1-yl-acetic acid and 30.96 mmol of 3,4-dihydro-3-hydroxy-4-oxo-1,2,3-benzotriazine (DHBT-OH) in 100 ml of absolute DMF, 32.51 mmol of dicyclohexyl carbodiimide are added, and this solution is stirred for 1 h at 40° C. Subsequently, 23.84 mmol of (2R)-2-[2-(tert.-butoxycarbonylamino) ethyl]-amino-4-(diethoxy-phosphoryl) butyric acid methyl ester are added and stirred at 40° C. The reaction is monitored by HPLC and is completed after 3 days.

The solution is separated from insoluble parts by filtration, and the solvent is removed in vacuo. The residue is solved in dichloromethane and is stored overnight in a refrigerator. In this process, further dicyclohexyl urea precipitates which is separated by filtration. The filtrate is washed two or three times with diluted sodium bicarbonate solution (⅓ saturated sodium bicarbonate solution, ⅔ water), one or two times with diluted potassium hydrogen sulfate solution (⅓ saturated potassium hydrogen sulfate solution, ⅔ water), dried over MgSO$_4$ and concentrated by means of a rotating evaporator. The further purification is carried out by solving in acetic acid ethyl ester and storing overnight in the refrigerator, whereupon further optionally precipitated dicyclohexyl urea is separated by filtration and the solvent is removed again. The crude product is then solved in dichloromethane (5 ml for 3 g crude product each), and again precipitated with diethyl ether (25 ml for 3 g crude product each) and hexane (5 ml for 3 g crude product each). The solvent with the impurities is removed and the product is dried in vacuo.

Yield: about 65% of a bright yellow solid $^1$H-NMR (CDCl$_3$): 1.32 (t, 6H, P(O)(OCH$_2$CH$_3$)$_2$); 1.44 (s, 9H, C(CH$_3$)$_3$); 1.75-2.45 (m, 4H, CHCH$_2$CH$_2$P); 3.2-3.85 (m, 4H, NCH$_2$CH$_2$N); 3.73 (s, 3H, OCH$_3$); 4.07 (m, 4H, P(O)(OCH$_2$CH$_3$)$_2$); 4.28 (m, 1H, NCHC(O)); 4.42/4.99 (2d, 2H, NCH$_2$C(O)); 5.22 (s, 2H, OCH$_2$Ph); 5.56 (t, br, 1H, C(O)NHCH$_2$); 7.25 (d, 1H, CCH=CHN); 7.38 (s, 5H, Ph); 7.55 (d, 1H, CCH=CHN).

Example 8
Production of (R)-2-([2-{N4-benzyloxycarbonylamino-cytosin-1-yl}-acetyl]-[2-tert.-butoxycarbonylamino-ethyl]amino)-4-(diethoxy-phosphoryl) butyric acid

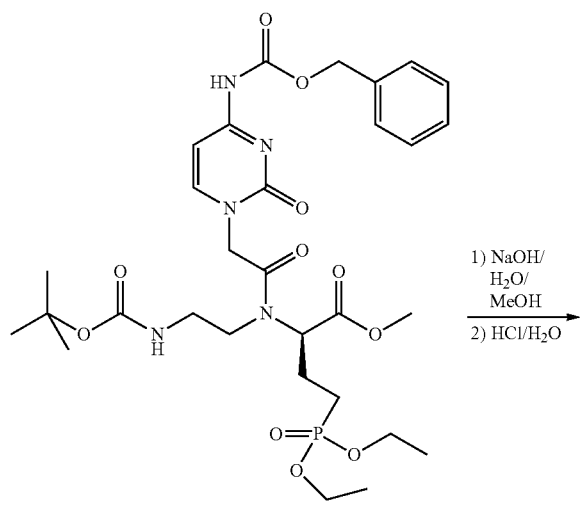

1) NaOH/ H$_2$O/ MeOH
2) HCl/H$_2$O

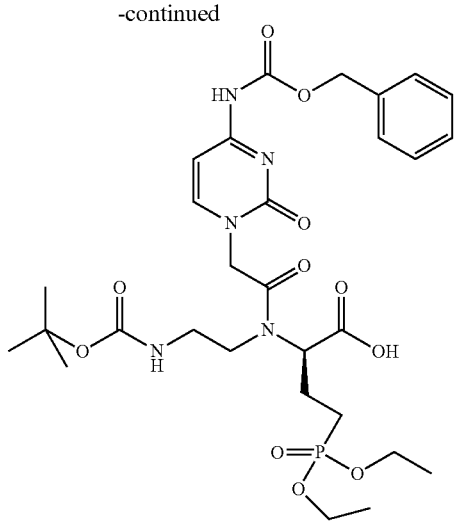

19.1 mmol of (R)-2-([2-{N4-benzyloxycarbonylcytosin-1-yl}-acetyl]-[2-tert.-butoxycarbonylamino-ethyl]-amino)-4-(diethoxy-phosphoryl) butyric acid methyl ester are solved in 80 ml of THF and water (2:3) and cooled to 0° C. To this solution, 48 ml of a 1 M solution of lithium hydroxide are added in drops (pH ~9). The progress of the reaction is monitored by means of DC (10% methanol in dichloromethane). After completion of the reaction, the reaction solution is diluted with 130 ml water and sodium chloride solution and once extracted with dichloromethane (200 ml). The aqueous phase is adjusted with 2 M potassium hydrogen sulfate solution to a pH value of 2-3, and several times extracted with dichloromethane. Thereby, the pH value is controlled and optionally corrected again and again. The combined organic phases are dried over MgSO$_4$, and the solvent is removed in vacuo. If necessary, the crude product can be reprecipitated from dichloromethane with diethyl ether. Finally, the product is dried by a lyophylisator.

Yield: about 80% of a white yellow solid $^1$H-NMR (DMSO-d$_6$): 1.21 (t, 6H, P(O)(OCH$_2$CH$_3$)$_2$); 1.39 (s, 9H, C(CH$_3$)$_3$); 1.70-2.30 (m, 4H, CHCH$_2$CH$_2$P); 2.90-3.60 (m, 4H, NCH$_2$CH$_2$N); 3.93-4.02 (m, 4H, P(O)(OCH$_2$CH$_3$)$_2$); 4.25 (m, 1H, NCHC(O)); 4.50-4.83 (m, 2H, NCH$_2$C(O)); 5.19 (s, 2H, OCH$_2$Ph); 6.88 (m, br, 1H, C(O)NHCH$_2$); 7.02 (d, 1H, CCH=CHN); 7.31-7.41 (m, 5H, Ph); 7.97 (d, 1H, CCH=CHN).

Example 9

Production of Further Compounds of the General Formula II

By analogous syntheses as described in the examples 7 and 8, wherein despite of C(Z)—CH$_2$—COOH further Z protected, benzyl protected (Bzl), anisoyl protected (An) or acetyl protected (Ac), respectively, and unprotected nucleobase acetic acid components, such as A(Z)—CH$_2$—COOH, A(An)-CH$_2$—COOH, A(Bzl)-CH$_2$—COOH, G(Z)—CH$_2$—COOH, G(Ac)-CH$_2$—COOH, C(An)-CH$_2$—COOH, C(Bzl)-CH$_2$—COOH, J(Z)—CH$_2$—COOH, J(Bzl)-CH$_2$—COOH, J(An)-CH$_2$—COOH or T-CH$_2$—COOH, respectively, (A=adeninyl, C=cytosinyl, G=guaninyl, T=thyminyl; J=pseudoisocytosinyl) as well as phenylacetic acid are used, further compounds of the general formula II according to the invention are produced.

A$^R$(Z):
$^1$H-NMR (CH$_3$OH-d$_4$): 1.20 (t, 6H, P(O)(OCH$_2$CH$_3$)$_2$); 1.34 (s, 9H, C(CH$_3$)$_3$); 1.70-2.30 (m, 4H, CHCH$_2$CH$_2$P); 3.00-3.80 (m, 4H, NCH$_2$CH$_2$N); 3.93-4.02 (m, 4H, P(O)(OCH$_2$CH$_3$)$_2$); 4.10 (m, 1H, NCHC(O)); 5.18 (s, 2H, OCH$_2$Ph); 5.20-5.40 (m, 2H, NCH$_2$C(O)); 7.15-7.40 (m, 5H, Ph); 8.14 (s, 1H, N=CHN); 8.46 (s, 1H, N=CHN).

A$^R$(Bzl):
$^1$H-NMR (DMSO-d$_6$): 1.21 (t, 6H, P(O)(OCH$_2$CH$_3$)$_2$); 1.40 (s, 9H, C(CH$_3$)$_3$); 1.70-2.20 (m, 4H, CHCH$_2$CH$_2$P,); 2.90-3.75 (m, 4H, NCH$_2$CH$_2$N); 3.90-4.10 (m, 4H, P(O)(OCH$_2$CH$_3$)$_2$); 4.22 (m, 1H, NCHC(O)); 5.25-5.45 (m, 2H, NCH$_2$C(O)); 6.96 (m, br, 1H, C(O)NHCH$_2$); 7.50-8.10 (m, 5H, Ph); 8.42 (s, 1H, N=CHN); 8.69 (s, 1H, N=CHN).

A$^R$(An):
$^1$H-NMR (DMSO-d$_6$): 1.21 (t, 6H, P(O)(OCH$_2$CH$_3$)$_2$); 1.41 (s, 9H, C(CH$_3$)$_3$); 1.70-2.20 (m, 4H, CHCH$_2$CH$_2$P); 2.90-3.750 (m, 4H, NCH$_2$CH$_2$N); 3.86 (s, 3H, OCH$_3$); 3.90-4.10 (m, 4H, P(O)(OCH$_2$CH$_3$)$_2$); 4.22 (m, 1H, NCHC(O)); 5.25-5.45 (m, 2H, NCH$_2$C(O)); 6.96 (m, br, 1H, C(O)NHCH$_2$); 7.08 (d, 2H, Ph); 8.05 (d, 2H, Ph); 8.42 (s, 1H, N=CHN); 8.69 (s, 1H, N=CHN).

J$^R$(Z):
$^1$H-NMR (DMSO-d$_6$): 1.32 (t, 6H, P(O)(OCH$_2$CH$_3$)$_2$), 1.42 (s, 9H, C(CH$_3$)$_3$); 1.60-2.50 (m, 4H, CHCH$_2$CH$_2$P,); 3.10-3.55 (m, 4H, NCH$_2$CH$_2$N); 3.65-3.90 (m, 2H, NCH$_2$C(O)); 4.00-4.15 (m, 4H, P(O)(OCH$_2$CH$_3$)$_2$); 4.20 (m, 1H, NCHC(O)); 5.24 (s, 2H, OCH$_2$Ph); 6.80 (m, br, 1H, C(O)NHCH$_2$); 7.27 (d, 1H, C=CHN); 7.30-7.50 (m, 5H, Ph).

J$^R$(An):
$^1$H-NMR (DMSO-d$_6$): 1.22 (t, 6H, P(O)(OCH$_2$CH$_3$)$_2$); 1.38 (s, 9H, C(CH$_3$)$_3$); 1.65-2.25 (m, 4H, CHCH$_2$CH$_2$P); 2.80-3.70 (m, 4H, NCH$_2$CH$_2$N); 2.80-3.70 (m, 2H, CCH$_2$C(O)); 3.84 (s, 3H, OCH$_3$); 3.90-4.05 (m, 4H, P(O)(OCH$_2$CH$_3$)$_2$); 4.17 (m, 1H, NCHC(O)); 6.81 (m, br, 1H, C(O)NHCH$_2$); 7.05 (d, 2H, Ph); 7.70 (s, 1H, NCH=C); 8.07 (d, 2H, Ph).

G$^R$(Z):
$^1$H-NMR (DMSO-d$_6$): 1.18 (t, 6H, P(O)(OCH$_2$CH$_3$)$_2$), 1.37 (s, 9H, C(CH$_3$)$_3$); 1.70-2.30 (m, 4H, CHCH$_2$CH$_2$P,); 2.95-3.70 (m, 4H, NCH$_2$CH$_2$N); 3.90-4.10 (m, 4H, P(O)(OCH$_2$CH$_3$)$_2$); 4.20 (m, 1H, NCHC(O)); 4.85-5.20 (m, 2H, NCH$_2$C(O)); 5.269 (s, 2H, OCH$_2$Ph); 6.95 (m, br, 1H, C(O)NHCH$_2$); 7.30-7.50 (m, 5H, Ph); 7.85 (s, 1H, N=CHN).

G$^R$(Ac):
$^1$H-NMR (DMSO-d$_6$): 1.20 (t, 6H, P(O)(OCH$_2$CH$_3$)$_2$); 1.41 (s, 9H, C(CH$_3$)$_3$); 1.70-2.18 (m, 4H, CHCH$_2$CH$_2$P); 2.20 (s, 3H, CH$_3$C(O)); 2.90-3.60 (m, 4H, NCH$_2$CH$_2$N); 3.90-4.10 (m, 4H, P(O)(OCH$_2$CH$_3$)$_2$); 4.22 (m, 1H, NCHC(O)); 4.91-5.22 (m, 2H, NCH$_2$C(O)); 7.00 (m, br, 1H, C(O)NHCH$_2$); 7.88 (s, 1H, N=CH—N).

C$^R$(Bzl):
$^1$H-NMR (DMSO-d$_6$): 1.21 (t, 6H, P(O)(OCH$_2$CH$_3$)$_2$); 1.40 (s, 9H, C(CH$_3$)$_3$); 1.70-2.30 (m, 4H, CHCH$_2$CH$_2$P); 3.20-3.60 (m, 4H, NCH$_2$CH$_2$N); 3.93-4.02 (m, 4H, P(O)(OCH$_2$CH$_3$)$_2$); 4.28 (m, 1H, NCHC(O)); 4.50-4.83 (m, 2H, NCH$_2$C(O)); 6.90 (m, br, 1H, C(O)NHCH$_2$); 7.33 (d, 1H, CCH=CHN); 7.50-7.55 (m, 2H, Ph); 7.62 (d, 1H, CCH=CHN); 8.00-8.10 (m, 3H, Ph).

C$^R$(An):
$^1$H-NMR (DMSO-d$_6$): 1.22 (t, 6H, P(O)(OCH$_2$CH$_3$)$_2$); 1.39 (s, 9H, C(CH$_3$)$_3$); 1.65-2.10 (m, 4H, CHCH$_2$CH$_2$P); 3.20-3.60 (m, 4H, NCH$_2$CH$_2$N); 3.84 (s, 3H, OCH$_3$); 3.85-4.05 (m, 4H, P(O)(OCH$_2$CH$_3$)$_2$); 4.25 (m, 1H, NCHC(O)); 4.50-4.95 (m, 2H, NCH$_2$C(O)); 6.90 (m, br, 1H, C(O)NHCH$_2$); 7.04 (d, 2H, Ph); 7.30 (d, 1H, CCH=CHN); 8.00 (d, 1H, CCH=CHN); 8.03 (d, 2H, Ph).

T$^R$:
$^1$H-NMR (DMSO-d$_6$): 1.22 (t, 6H, P(O)(OCH$_2$CH$_3$)$_2$); 1.39 (s, 9H, C(CH$_3$)$_3$); 1.65-2.20 (m, 4H, CHCH$_2$CH$_2$P); 1.75 (s, 3H, C=CCH$_3$); 2.90-3.50 (m, 4H, NCH$_2$CH$_2$N); 3.90-4.10 (m, 4H, P(O)(OCH$_2$CH$_3$)$_2$); 4.18 (m, 1H, NCHC(O)); 4.45-4.65 (m, 2H, NCH$_2$C(O)); 6.86 (m, br, 1H, C(O)NHCH$_2$); 7.37 (s, 1H, NCH=C).

P$^R$:
$^1$H-NMR (DMSO-d$_6$): 1.20 (t, 6H, P(O)(OCH$_2$CH$_3$)$_2$); 1.38 (s, 9H, C(CH$_3$)$_3$); 1.46-2.30 (m, 4H, CHCH$_2$CH$_2$P); 3.00-3.45 (m, 4H, NCH$_2$CH$_2$N); 3.50-3.75 (m, 2H, CCH$_2$C(O)); 3.80-4.00 (m, 4H, P(O)(OCH$_2$CH$_3$)$_2$); 4.22 (m, 1H, NCHC(O)); 7.10-7.30 (m, 5H, Ph).

Example 10

Production of Further Compounds of the General Formula II with S Configuration at the Asymmetric Center The production method for the compounds of the general formula II with R configuration is applied analogically for the production of the corresponding compounds of the general formula II with S configuration. Here, (R)-2,5-dihydro-3,6-dimethoxy-2-isopropyl pyrazine is used as a starting material in the synthesis described in example 1, and the following syntheses are carried out analogically as described.

For example, the following compound was produced:

J$^S$(Z):
$^1$H-NMR (DMSO-d$_6$): 1.32 (t, 6H, P(O)(OCH$_2$CH$_3$)$_2$), 1.42 (s, 9H, C(CH$_3$)$_3$); 1.60-2.50 (m, 4H, CHCH$_2$CH$_2$P,); 3.10-3.55 (m, 4H, NCH$_2$CH$_2$N); 3.65-3.90 (m, 2H, NCH$_2$C(O)); 4.00-4.15 (m, 4H, P(O)(OCH$_2$CH$_3$)$_2$); 4.20 (m, 1H, NCHC(O)); 5.24 (s, 2H, OCH$_2$Ph); 6.80 (m, br, 1H, C(O)NHCH$_2$); 7.27 (d, 1H, C=CHN); 7.30-7.50 (m, 5H, Ph).

Example 11

General Synthesis Specification for Compounds According to the Invention with a MNPA Substitutent at the Rest K By sequential connection of corresponding compounds of the general formula II having an asymmetric center and/or corresponding compounds of the general formula II having no asymmetric center and/or amino acids and/or amino acid derivatives and/or fluorescence markers by means of solid phase peptide synthesis, the compounds according to the invention are produced.

In this context, the following synthesis protocol is applied:
Step 1: 3 h Preswelling of 10 mg of resin (Boc-Gly-PAM-MBHA resin, 0.54 mmol/g) in dichloromethane.
Step 2: Start of the synthesis cycle: 4× washing with dichloromethane.
Step 3: Cleavage of the Boc group by reaction with TFA and m-cresol (95:5). Reaction period: 2×3 min in each case.
Step 4: 5× Washing with dichloromethane.
Step 5: 5× Washing with NMP.
Step 6: 1 min Preactivation of 4 equivalents of the corresponding protected compound of the general formula II, or of a correspondingly protected amino acid, respectively, with 3.8 equivalents of HATU and 9 equivalents of NMM in NMP and pyridine (2:1).
Step 7: Reaction of the activated protected compound of the general formula II, or of a correspondingly protected amino acid, respectively, with the solid phase; (1. coupling; period of time: 30 min).

Step 8: 4× Washing with NMP.
Step 9: 1× Washing with dichloromethane.
Step 10: Repetition of steps 6 to 8 (2. coupling).
Step 11: Examination of the efficiency of the coupling with ninhydrin (Kaiser's test; if the Kaiser's test shows a positive result, the steps 6 to 8 have to be repeated with the corresponding protected compound of the general formula II).
Step 12: After a negative Kaiser's test, the reaction sequence is capped two times with a solution of $Ac_2O$, NMP and pyridin (1:25:25) for 4 min in each case.
Step 13: 5× Washing with NMP.
Step 14: Repeating of the synthesis cycles (steps 2 to 13) up to the coupling with the final corresponding protected compound of the general formula II. Subsequently, the synthesis cycles are optionally repeated (steps 2 to 13) up to the coupling with the final correspondingly protected amino acid.
Step 15: 4× Washing with dichloromethane.
Step 16: Cleaving of the Boc group by reaction with TFA and m-cresole (95:5). Reaction period: 2×3 min in each case.
Step 17: 5× Washing with dichloromethane.
Step 18: 5× Washing with NMP.
Step 19: 1 min Preactivation of 6 equivalents of MNPA-OH with 5.7 equivalents of HATU and 13 equivalents of NMM in NMP and pyridine (2:1).
Step 20: Reaction of activated MNPA-OH with the solid phase (time period: 30 min).
Step 21: 4× Washing with NMP.
Step 22: Repetition of steps 19 to 21 (2. coupling).
Step 23: 5× Washing with dichloromethane.
Step 24: For drying: 5× washing with diethyl ether.

A compound of the general formula I is obtained that is bound to the resin at the carboxylic acid terminal end.

Cleavage of the Compound According to the Invention from the Resin:

The resin with the compound according to the invention is stirred in an aqueous ammonia solution (28-30 weight percent $NH_3$ in $H_2O$) at 60° C. for 20 h. The cleaved resin is subsequently filtered, and the filtrate is concentrated in vacuo and dried. The crude product is purified by preparative HPLC over a RP-C18 column with methanol and water. The compound according to the invention is obtained as a colorless solid in a yield of about 50%. The molecular weight of the compound according to the invention is characterized by MALDI-TOF.

Example 12

General Synthesis Specification for Compounds According to the Invention with a DNPA Substituent at the Rest K By sequential connection of corresponding compounds of the general formula II having an asymmetric center and/or corresponding compounds of the general formula II having no asymmetric center and/or amino acids and/or amino acid derivatives and/or fluorescence markers by means of solid phase peptide synthesis, the compounds according to the invention are produced.

Thereby, the following synthesis protocol is applied:
Step 1: Preswelling of 10 mg resin for 3 hours (Boc-Gly-PAM-MBHA resin, 0.54 mmol/g) in dichloromethane.
Step 2: Start of the synthesis cycle: 4× washing with dichloromethane.
Step 3: Cleavage of the Boc group by reaction with TFA and m-cresol (95:5). Reaction period: 2×3 min in each case.
Step 4: 5× Washing with dichloromethane.
Step 5: 5× Washing with NMP.
Step 6: 1 min Preactivation of 4 equivalents of the corresponding protected compound of the general formula II, or of a correspondingly protected amino acid, respectively, with 3.8 equivalents of HATU and 9 equivalents of NMM in NMP and pyridine (2:1).
Step 7: Reaction of the activated protected compound of the general formula II, or of a correspondingly protected amino acid, respectively, with the solid phase (1. coupling; time period: 30 min).
Step 8: 4× Washing with NMP.
Step 9: 1× Washing with dichloromethane.
Step 10: Repetition of steps 6 to 8 (2. coupling).
Step 11: Examination of the efficiency of the coupling with ninhydrin (Kaiser's test; if the Kaiser's test shows a positive result, the steps 6 to 8 have to be repeated with the corresponding protected compound of the general formula II).
Step 12: After a negative Kaiser's test, the reaction sequence is capped twice with a solution of $Ac_2O$, NMP, and pyridine (1:25:25) for 4 min each.
Step 13: 5× Washing with NMP.
Step 14: Repeating of the synthesis cycles (steps 2 to 13) up to the coupling with the final corresponding protected compound of the general formula II. Thereafter, the synthesis cycles (steps 2 to 13) optionally are repeated up to the coupling with the final correspondingly protected amino acid.
Step 15: 4× Washing with dichloromethane.
Step 16: Cleavage of the Boc group by reaction with TFA and m-cresol (95:5). Reaction period: 2×3 min in each case.
Step 17: 5× Washing with dichloromethane.
Step 18: 5× Washing with NMP.
Step 19: 1 min Preactivation of 6 equivalents of DNPA-OH with 5.7 equivalents of HATU and 13 equivalents of NMM in NMP and pyridine (2:1).
Step 20: Reaction of activated DNPA-OH with the solid phase (time period: 30 min).
Step 21: 4× Washing with NMP.
Step 22: Repetition of steps 19 to 21 (2. coupling).
Step 23: 5× Washing with dichloromethane.
Step 24: For drying: 5× washing with diethyl ether.

A compound of the general formula I is obtained that is bound to the resin at the carboxylic acid terminal end.

Cleavage of the Compound According to the Invention from the Resin:

The resin with the compound according to the invention is stirred in an aqueous ammonia solution (28-30 weight percent $NH_3$ in $H_2O$) at 60° C. for 20 h. The cleaved resin then will be separated by filtration, and the filtrate is concentrated in vacuo and dried. The crude product is purified by preparative HPLC via a RP-18 column with methanol and water. The compound according to the invention is obtained as a colorless solid in a yield of about 50%. The molecular weight of the compound according to the invention is characterized by MALDI-TOF.

Example 13

General Synthesis Specification for the Compounds According to the Invention with a Linker and a MNPA Substituent or DNPA Substituent at the Rest K, Respectively By sequential connection of corresponding compounds of the general formula II having an asymmetric center and/or corresponding compounds of the general formula II having no asymmetric center and/or amino acids and/or amino acid derivatives and/or fluorescence markers as well as suitable linker monomers by means of solid phase peptide synthesis, the compounds according to the invention are produced.

Thereby, the following synthesis protocol is applied:

Synthesis Protocol:

Step 1: Preswelling of 10 mg resin for 3 hours (Boc-Gly-PAM-MBHA resin, 0.54 mmol/g) in dichloromethane.

Step 2: Start of the synthesis cycle: 4× washing with dichloromethane.

Step 3: Cleavage of the Boc group by reaction with TFA and m-cresole (95:5). Reaction period: 2×3 min in each case.

Step 4: 5× Washing with dichloromethane.

Step 5: 5× Washing with NMP.

Step 6: 1 min Preactivation of 4 equivalents of the corresponding protected compound of the general formula II, or of a correspondingly protected amino acid, respectively, with 3.8 equivalents of HATU and 9 equivalents of NMM in NMP and pyridine (2:1).

Step 7: Reaction of the corresponding protected compound of the general formula II, or of a correspondingly protected amino acid, respectively, with the solid phase (1. coupling; time period: 30 min).

Step 8: 4× Washing with NMP.

Step 9: 1× Washing with dichloromethane.

Step 10: Repetition of steps 6 to 8 (2. coupling).

Step 11: Examination of the efficiency of the coupling with ninhydrin (Kaiser's test; if the Kaiser's test shows a positive result, steps 6 to 8 have to be repeated with the corresponding protected compound of the general formula II).

Step 12: After a negative Kaiser's test, the synthesis sequence is capped twice with a solution of $Ac_2O$, NMP, and pyridine (1:25:25) for 4 min each.

Step 13: 5× Washing with NMP.

Step 14: Repetition of the synthesis cycle (steps 2 to 13) up to the coupling of the linker eg1 (8-amino-2,6-dioxaoctanoic acid).

Step 15: Coupling of the linkers: 4× washing with dichloromethane.

Step 16: Cleavage of the Boc group by reaction with TFA and m-cresol (95:5). Reaction period: 2×3 min in each case.

Step 17: 5× Washing with dichloromethane.

Step 18: 5× Washing with NMP.

Step 19: 1 min Preactivation of 4 equivalents eg1 with 3.8 equivalents of HATU and 9 equivalents of NMM in NMP and pyridine (2:1).

Step 20: Reaction of the activated linker with the solid phase (1. coupling; time period: 30 min).

Step 21: 4× Washing with NMP.

Step 22: 1× Washing with dichloromethane.

Step 23: Repetition of steps 19 to 21 (2. coupling).

Step 24: Examination of the efficiency of the coupling with ninhydrin (Kaiser's test; if the Kaiser's test shows a positive result, steps 19 to 21 have to be repeated).

Step 25: After a negative Kaiser's test, the reaction sequence is capped twice with a solution of $Ac_2O$, NMP, and pyridine (1:25:25) for 4 min each.

Step 26: 5× Washing with NMP.

Step 27: 2× Repetition of the synthesis steps (steps 15 to 26) for $(eg1)_3$.

Step 28: Repetition of the steps of synthesis cycle (steps 2 to 13) up to the coupling with the final corresponding protected compound of the general formula II.

Thereafter, the steps of the synthesis cycle (Steps 2 to 13) optionally are repeated up to the coupling with the final correspondingly protected amino acid. Thereafter, in case of coupling of MNPA-OH, steps 15 to 24 from example 11, or in case of coupling of DNPA-OH, steps 15 to 24 from example 12, respectively, are performed.

A compound according to the invention having a linker is obtained that is bound to the resin at the carboxylic acid terminal end.

Cleavage of the Compound According to the Invention Having a Linker from the Resin:

The resin with the compound according to the invention with linker is stirred in an aqueous ammonia solution (28-30 weight percent $NH_3$ in $H_2O$) at 60° C. for 20 h. The cleaved resin is subsequently separated by filtration, and the filtrate is concentrated in vacuo and dried. The crude product is purified by preparative HPLC via a RP-C18 column with methanol and water. The compound according to the invention having a linker is obtained as a colorless solid in a yield of about 50%. The molecular weight of the compound according to the invention is characterized by MALDI-TOF.

Example 14

Further Examples of Sequences

By performance of the general synthesis specifications from the examples 11 or 12, further compounds according to the invention were produced:

MNPA-$A^R cG^R gT^R cG^R gC^R gA^R aC^R aT^R$-Gly-$NH_2$
MNPA-Bio-$A^R cG^R gT^R cG^R gC^R gA^R aC^R aT^R$-Gly-$NH_2$
  (Bio=lysine, functionalized with biotin via the amino function of the lysine side chain)
DNPA-$A^R cG^R gT^R cG^R gC^R gA^R aC^R aT^R$-Gly-$NH_2$
DNPA-Bio-$A^R cG^R gT^R cG^R gC^R gA^R aC^R aT^R$-Gly-$NH_2$
DNPA-t$G^R cC^R tA^R gG^R aC^R tC^R cA^R gC^R$-Gly-$NH_2$
DNPA-Bio-t$G^R cC^R tA^R gG^R aC^R tC^R cA^R gC^R$-Gly-$NH_2$
DNPA-t$G^R cC^R tA^R ggactC^R cA^R gC^R$-Gly-$NH_2$
DNPA-Bio-t$G^R cC^R tA^R ggactC^R cA^R gC^R$-Gly-$NH_2$
DNPA-c$G^R aA^R tA^R aG^R gA^R gG^R cT^R tA^R$-Gly-$NH_2$
DNPA-Bio-c$G^R aA^R tA^R aG^R gA^R gG^R cT^R tA^R$-Gly-$NH_2$
DNPA-c$G^R aA^R tA^R aggagG^R cT^R tA^R$-Gly-$NH_2$
DNPA-Bio-c$G^R aA^R tA^R aggagG^R cT^R tA^R$-Gly-$NH_2$
DNPA-g$G^R cT^R cG^R aA^R tA^R aG^R gA^R gG^R$-Gly-$NH_2$
DNPA-Bio-g$G^R cT^R cG^R aA^R tA^R aG^R gA^R gG^R$-Gly-$NH_2$
DNPA-g$G^R cT^R cG^R aataaG^R gA^R gG^R$-Gly-$NH_2$
DNPA-Bio-g$G^R cT^R cG^R aataaG^R gA^R gG^R$-Gly-$NH_2$
DNPA-a$C^R aA^R aT^R gC^R aT^R gG^R gC^R tG^R$-Gly-$NH_2$
DNPA-Bio-a$C^R aA^R aT^R gC^R aT^R gG^R gC^R tG^R$-Gly-$NH_2$
DNPA-a$C^R aA^R aT^R gcatgG^R gC^R tG^R$-Gly-$NH_2$
DNPA-Bio-a$C^R aA^R aT^R gcatgG^R gC^R tG^R$-Gly-$NH_2$
DNPA-c$G^R cC^R tT^R aT^R cC^R gT^R aG^R cC^R$-Gly-$NH_2$
DNPA-Bio-c$G^R cC^R tT^R aT^R cC^R gT^R aG^R cC^R$-Gly-$NH_2$
DNPA-c$G^R cC^R tT^R atccgT^R aG^R cC^R$-Gly-$NH_2$
DNPA-Bio-c$G^R cC^R tT^R atccgT^R aG^R cC^R$-Gly-$NH_2$
DNPA-tgcc$T^R aG^R gactcC^R aG^R c$-Gly-$NH_2$
DNPA-Dota-g$G^R cT^R cG^R aA^R tA^R aG^R gA^R gG^R$-Gly-$NH_2$
  (DOTA=lysine, functionalized with DOTA via the amino function of the lysine side chain)

Example 15

Synthesis Specification for a Compound According to the Invention with the General Formula V 2 ml of DMF and 2 ml of pyridine are given in a screw cup. Under stirring, 382 mg (2.95 mmol) DIPEA, and subsequently, 291 mg (1.48 mmol) of 4-hydroxy-3-nitro-phenyl acetic acid are added. Subsequently, 562 mg (1.48 mmol) of HATU, solved in 2 ml of DMF, are added. The reaction mixture is allowed to preactivate for 5 min. The preactivated solution is added in drops to a solution of 500 mg (1.48 mmol) 2-(10-hydroxydecyl)-5,6-dimethoxy-3-methyl cyclohexa-2,5-diene-1,4-dione (Idebenone), solved in 10 ml of DMF, and subsequently heated to 40° C. After a reaction time of 24 h, the solvent is removed, and the residue is solved in acetic acid ethyl ester. The organic phase is washed twice with 2 N potassium hydrogen sulfate solution and once with saturated sodium chloride solution, and subsequently dried over magnesium sulfate. The crude product is purified by chromatography (silica gel, hexane and acetic acid ethyl ester, 1:1, v/v).

position of the mtDNA/mtRNA coding for the mitochondrial protein COX1, in different concentrations (100 nM, 250 nM, 500 nM, 1 µM, 2.5 µM, 5 µM and 10 µM) and for different periods of time (3, 6, 9, 11 and 17 days). In case of experiments which take more than 3 days, the supernatant is replaced every 3 days by fresh medium having each the same concentration of the compound according to the invention, DNPA-tG$^R$cC$^R$tA$^R$ggactC$^R$cA$^R$gC$^R$-Gly-NH$_2$.

The determination of the COX1 levels occurs by Western blotting against porin, a mitochondrial transmembrane protein, whose concentration is not influenced by the treatment

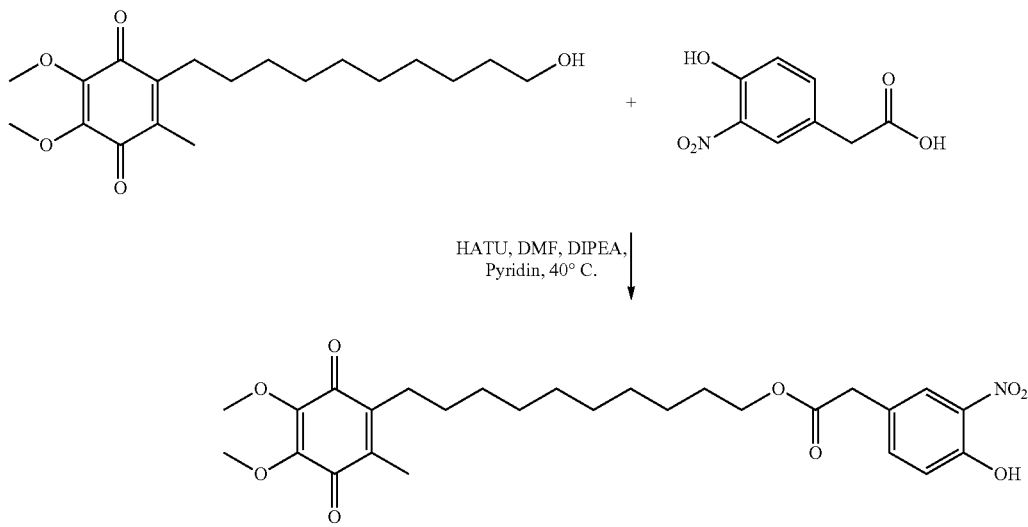 [SMILES: COC1=C(OC)C(=O)C(CCCCCCCCCCO)=C(C)C1=O ; "+" ; O=C(O)Cc1ccc(O)c([N+](=O)[O-])c1 ; COC1=C(OC)C(=O)C(CCCCCCCCCCOC(=O)Cc2ccc(O)c([N+](=O)[O-])c2)=C(C)C1=O]

Example 16

Selective Localization of Compounds of the General Formula I Bearing a Monohydroxy Mononitrophenyl Rest or a Monohydroxy Dinitrophenyl Rest, Respectively HeLa cells or 143B parental cells, respectively, are incubated with a solution of 10 µM biotin labeled compounds of the general formula I. After 24 h, a 2 µM MitoTracker solution is added, and after further 45 min, the cells are fixed with ethanol. Subsequently, a solution of fluorescein and avidin (5 µg/ml) is allowed to act on the cells for 30 min at room temperature. After washing the cells, a biotinylated anti-avidin solution (5 µg/ml) is allowed to act on the cells for 30 min at room temperature. After a further washing of the cells, a solution of fluorescein and avidin (5 µg/ml) is again allowed to act on the cells for 30 min at room temperature. After further washing steps, the cell nucleus is marked by DAPI counter staining. Subsequently, the steric distribution or dispersion of the compounds of the general formula I, of the mitochondria, as well as of the cell nuclei within the cells are investigated by a confocal microscope.

Example 17

Reduction of COX1 and Amount of mtDNA in Hela Cells by Treatment with the Compound According to the Invention, DNPA-tG$^R$cC$^R$tA$^R$ggactC$^R$cA$^R$gC$^R$-Gly-NH$_2$ HeLa cells are incubated with a solution of DNPA-tG$^R$c-C$^R$tA$^R$ggactC$^R$cA$^R$gC$^R$-Gly-NH$_2$ ("effective"), directed to a with the compound according to the invention, as an internal standard. The reduction of COX1 is presented in comparison with untreated HeLa cells. In this context, the COX1 concentration of the untreated HeLa cells is defined as 100%.

At a concentration of 10 µM of the compound according to the invention, the COX1 level in the HeLa cells is reduced to 67% after 3 days, and to 20% after 9 days.

The following table shows the dependency of the concentration of COX1 reduction after a treatment period of 9 days:

| | concentration [µM] | | | | | | |
| --- | --- | --- | --- | --- | --- | --- | --- |
| | 10 | 5 | 2.5 | 1 | 0.5 | 0.25 | 0.1 |
| COX1 [%] | 20 | 48 | 55 | 75 | 80 | 88 | 100 |

The determination of the amount of mtDNA takes place by real-time PCR against the DNA of the cell nucleus which is not influenced by the treatment with the compound according to the invention, DNPA-tG$^R$cC$^R$tA$^R$ggactC$^R$cA$^R$gC$^R$-Gly-NH$_2$, as an internal standard. The reduction of mtDNA is presented in comparison to the untreated HeLa cells. In this context, the amount of mtDNA of untreated HeLa cells is defined as 100%. As a further comparison, a compound according to the invention without the complementary sequence to mtDNA/mtRNA is used ("negative control").

At a concentration of the compound according to the invention DNPA-tG$^R$cC$^R$tA$^R$ggactC$^R$cA$^R$gC$^R$-Gly-NH$_2$ of 10 µM, no effect can be assessed still after 3 days. After 6 days, a reduction of the mtDNA to 81%, and after 9 days to 62% can be observed, in comparison with untreated HeLa cells or in comparison with HeLa cells treated with a negative control, respectively. Thereafter, the value of the amount of the reduced mtDNA is also constant after 11 days (64%), and 17 days (61%).

The following table shows the concentration dependency of the reduction of mtDNA after a treatment of 9 days with the effective compound according to the invention, in comparison with the negative control:

| | Concentration [μM] | | | | | | |
|---|---|---|---|---|---|---|---|
| | 10 | 5 | 2.5 | 1 | 0.5 | 0.25 | 0.1 |
| mtDNA [%] "effectiv" | 62 | 60 | 82 | 81 | 84 | 101 | 97 |
| mtDNA [%] "negative control" | 93 | 101 | 99 | 97 | 110 | 94 | 94 |

The invention claimed is:

1. A compound of the formula I,

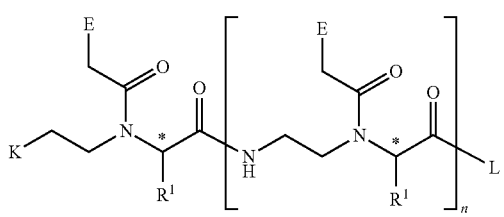

wherein;
n represents an integer from 0 to 35;
each E, independently of each other, represents:
a hydrogen atom;
a substituted or unsubstituted phenyl group;
a substituted or unsubstituted heterocycle;
a nucleobase, optionally substituted with protecting groups; or
a DNA intercalator;
each $R^1$, independently of each other, represents:
a hydrogen atom or a side chain of a naturally occurring or non-naturally occurring amino acid; or
an optionally substituted alkyl, alkenyl, alkylaryl, aryl, heterocyclic or alicyclic group having up to 20 carbon atoms;
wherein at least one of the optionally substituted alkyl, alkenyl, alkylaryl, aryl, heterocyclic or alicyclic groups, having up to 20 carbon atoms, is substituted with one or more phosphonic acid ester functions or phosphononic acid functions;
K represents a group of the formula $-NR^2R^3$, $-N^{\oplus}R^2R^3R^4$, $-NR^2(CO)R^3$ or $-NR^2(CS)R^3$
wherein $R^2$, $R^3$ and $R^4$, independently of each other, represent:
a hydrogen atom; an alkyl, alkaryl, alkenyl, or alkenyl group; an amino protecting group; a reporter ligand; a fluorescence marker; an intercalator; a chelator; an amino acid; a peptide; a protein; a carbohydrate; a lipid; a steroid; a fatty acid; an oligonucleotide; a quantum dot; a FRET quencher (fluorescence resonance energy transfer quencher); or a polymer soluble or insoluble in water;
wherein each of the above mentioned groups optionally may be substituted;

L represents a group of the formula $-NR^5R^6$, $-NR^5(CO)R^6$, $-NR^5(CS)R^6$, $-OR^7$ or $-SR^7$
wherein $R^5$ and $R^6$, independently of each other, represent:
a hydrogen atom; an alkyl, alkaryl, alkenyl, or alkinyl group; a reporter ligand; a fluorescence marker; an intercalator; a chelator; an amino acid; an amino acid amide; a peptide; a peptide amide; a protein; a carbohydrate; a lipid; a steroid; a fatty acid; an oligonucleotide; a quantum dot; a FRET quencher (fluorescence resonance energy transfer quencher); or a polymer soluble or insoluble in water; and
wherein $R^7$ represents:
a hydrogen atom; an alkyl group; a reporter ligand; a fluorescence marker; an intercalator; a chelator; an amino acid; an amino acid amide; a peptide; a peptide amide; a protein; a carbohydrate; a lipid; a steroid; a fatty acid; an oligonucleotide; a quantum dot; a FRET quencher; or a polymer soluble or insoluble in water;
wherein each of the above mentioned groups optionally may be substituted;
wherein the K, L or $R^1$ groups, independently of each other, are substituted with at least one monohydroxy mononitrophenyl group or monohydroxy dinitrophenyl group.

2. The compound according to claim 1;
wherein the compound according to formula I exhibits at least one asymmetric center.

3. The compound according to claim 1;
wherein at least one $R^1$ group does not represent a hydrogen atom; and
the compound according to formula I exhibits at least one asymmetric center.

4. The compound according to claim 1;
wherein each second $R^1$ group, independently of each other, represents an optionally substituted alkyl, alkenyl, alkylaryl, aryl, heterocyclic or alicyclic group having up to 20 carbon atoms, and;
the remaining $R^1$ groups represent hydrogen atoms.

5. The compound according to claim 1;
wherein each third group, independently of each other, represents an optionally substituted alkyl, alkenyl, alkylaryl, aryl-, heterocyclic or alicyclic group having up to 20 carbon atoms, and;
the remaining $R^1$ groups represent hydrogen atoms.

6. The compound according to claim 1;
wherein two, three, or more adjacent $R^1$ groups, independently of each other, represent optionally substituted alkyl, alkenyl, alkylaryl, aryl, heterocyclic or alicyclic groups having up to 20 carbon atoms;
and the remaining $R^1$ groups represent hydrogen atoms.

7. The compound according to claim 1;
wherein each $R^1$, independently of each other, represents an optionally substituted alkyl, alkenyl, alkylaryl, aryl, heterocyclic or alicyclic group having up to 20 carbon atoms.

8. The compound according to claim 1;
wherein one or more of the $R^1$ groups, independently of each other, represent phosphonic acid ester functions or phosphonic acid functions.

9. The compound according to claim 1;
wherein all asymmetric centers exhibit the same configuration.

10. The compound according to claim 1;
wherein all asymmetric centers exhibit a (S) configuration.

11. The compound according to claim 1;
wherein all asymmetric centers exhibit a (R) configuration.

12. The compound according to claim 1;
wherein each $R^1$, independently of each other, exhibits one or more phosphonic acid ester functions or phosphonic acid functions;
wherein the phosphonic acid ester functions have the formula —P(=O)(OV)$_2$ or —P(=O)(OV)(OH);
wherein each V, independently of each other, represents an unsubstituted alkyl, alkenyl, alkylaryl, aryl or alicyclic group having up to 20 carbon atoms.

13. The compound according to claim 12;
wherein each V, independently of each other, represents a methyl, ethyl, cyclohexyl or benzyl group.

14. A compound containing at least two compounds according to claim 1;
wherein the compounds according to claim 1 are connected to each other via a linker.

15. The compound according to claim 14;
wherein the linker represents an alkyl chain, a peptide, an oligonucleotide or an oligomer that is composed of at least three units of 8-amino-3,6-dioxaoctanoic acid.

16. A composition containing at least one compound according to claim 1.

17. A pharmaceutical composition containing at least one compound or composition according to claim 1, optionally in combination with at least one carrier, solvent or other pharmaceutical adjuvant.

18. A method for the treatment of mitochondrial diseases selected from the group consisting of diabetes, Parkinson's disease and arteriosclerosis comprising:
administering a compound according to claim 1 to a subject in need thereof.

* * * * *